(12) United States Patent
Daniel et al.

(10) Patent No.: US 8,845,635 B2
(45) Date of Patent: Sep. 30, 2014

(54) DEVICE AND METHOD FOR THERMAL ABLATION OF BIOLOGICAL TISSUE USING SPHERICAL ABLATION PATTERNS

(75) Inventors: Steven A. Daniel, Fremont, CA (US);
David L. Morris, Fremont, CA (US);
Kee Sein Lee, Newark, CA (US)

(73) Assignee: S.D.M.H. PTY. Ltd., Sydney (AU)

( * ) Notice: Subject to any disclaimer, the term of this patent is extended or adjusted under 35 U.S.C. 154(b) by 1062 days.

(21) Appl. No.: 11/335,301

(22) Filed: Jan. 18, 2006

(65) Prior Publication Data
US 2006/0212032 A1    Sep. 21, 2006

Related U.S. Application Data

(60) Provisional application No. 60/644,722, filed on Jan. 18, 2005.

(51) Int. Cl.
*A61B 18/14* (2006.01)
*A61B 18/00* (2006.01)

(52) U.S. Cl.
CPC ....... *A61B 18/148* (2013.01); *A61B 2018/1425* (2013.01); *A61B 2018/00267* (2013.01); *A61B 2018/1475* (2013.01); *A61B 2018/0016* (2013.01); *A61B 2018/1432* (2013.01); *A61B 2018/143* (2013.01); *A61B 18/1477* (2013.01)
USPC .............................................. 606/50; 606/41

(58) Field of Classification Search
CPC ............. A61B 18/1477; A61B 18/148; A61B 18/1487; A61B 2018/0016; A61B 2018/00214; A61B 2018/00267; A61B 2018/1425; A61B 2018/143; A61B 2018/1432; A61B 2018/1467; A61B 2018/1475
USPC ................................. 606/41, 48, 50
See application file for complete search history.

(56) References Cited

U.S. PATENT DOCUMENTS

| | | | |
|---|---|---|---|
| 4,346,715 A | | 8/1982 | Gammell |
| 5,536,267 A | | 7/1996 | Edwards |
| 5,545,193 A | | 8/1996 | Fleischman |
| 5,582,609 A | * | 12/1996 | Swanson et al. ................ 606/39 |
| 5,672,174 A | | 9/1997 | Gough |
| 5,673,695 A | * | 10/1997 | McGee et al. ................ 600/374 |
| 5,683,384 A | | 11/1997 | Gough |
| 5,728,143 A | | 3/1998 | Gough |
| 5,800,484 A | | 9/1998 | Gough |
| 5,925,042 A | | 7/1999 | Gough |
| 5,938,694 A | | 8/1999 | Jaraczewski |
| 5,980,517 A | | 11/1999 | Gough |
| 6,001,093 A | | 12/1999 | Swanson |
| 6,050,995 A | * | 4/2000 | Durgin ........................... 606/47 |
| 6,059,780 A | | 5/2000 | Gough |
| 6,071,280 A | | 6/2000 | Edwards |

(Continued)

*Primary Examiner* — Michael Peffley
*Assistant Examiner* — Samantha Good
(74) *Attorney, Agent, or Firm* — Gregory & Sawrie LLP

(57) ABSTRACT

A tissue ablation device and method for tissue ablation are described. The tissue ablation device comprises an energy source and an introducer coupled to the energy source, the introducer having a body, a proximal end, and a distal end. The introducer carries an electrode array that comprises a plurality of electrodes, each electrode of the plurality of electrodes is configured to extend from the body of the introducer when moved from a retracted state to a deployed state. The electrode array is designed to encircle a portion of a target tissue when the electrodes are extended into the deployed state and to form a relatively spherical shaped ablation pattern in a tissue volume surrounding the target tissue when energized by the energy source.

15 Claims, 24 Drawing Sheets

(56) References Cited

U.S. PATENT DOCUMENTS

| | | | |
|---|---|---|---|
| 6,090,105 A * | 7/2000 | Zepeda et al. | 606/41 |
| 6,235,023 B1 | 5/2001 | Lee | |
| 6,330,478 B1 | 12/2001 | Lee | |
| 6,454,765 B1 | 9/2002 | Leveen | |
| 6,468,273 B1 | 10/2002 | Leveen | |
| 6,471,698 B1 | 10/2002 | Edwards | |
| 6,569,159 B1 | 5/2003 | Edwards | |
| 6,575,967 B1 | 6/2003 | Leveen | |
| 6,638,277 B2 | 10/2003 | Schaefer | |
| 6,858,025 B2 * | 2/2005 | Maurice | 606/21 |
| 6,958,062 B1 | 10/2005 | Gough | |
| 7,025,767 B2 | 4/2006 | Schaefer et al. | |
| 7,048,734 B1 * | 5/2006 | Fleischman et al. | 606/42 |
| 7,115,124 B1 * | 10/2006 | Xiao | 606/41 |
| 2003/0199862 A1 * | 10/2003 | Simpson et al. | 606/34 |

\* cited by examiner

DEVICE AND METHOD FOR THERMAL ABLATION OF BIOLOGICAL TISSUE USING SPHERICAL ABLATION PATTERNS

CROSS-REFERENCE TO RELATED APPLICATIONS

The current application claims the benefit of U.S. Provisional Patent Application 60/644,722, filed Jan. 18, 2005.

TECHNICAL FIELD

This invention relates generally to devices and methods for tissue ablation, and more particularly to devices for encircling target biological tissue.

BACKGROUND

Standard surgical procedures such as tissue resection for use in treatment of benign and malignant tumors of the liver and other organs have several key shortcomings affecting efficacy, morbidity and mortality. A fundamental issue in these shortcomings is the inability of the resection to be performed in a variety of cases. To help overcome this limitation a series of mono-polar radio frequency (RF) devices were designed for use in tissue ablation and resection. These mono-polar devices however have limited usefulness in typical clinical settings because they are overly complex and difficult to use, and result in time consuming procedures that can lead to auxiliary injury to patients through grounding pad burns. Further, these mono-polar tissue ablation devices are limited in the scope and size of the ablation that can be created, and exhibit poor consistency of ablative results along with an overall low efficiency. Typical known ablation devices are designed to pierce into that target tissue and ablate the tissue from the inside out. This method can result in uneven heating of the target tissue and result in tumor seeding due to repeated penetration and retraction from malignant tissue. Consequently, there is a need for a tissue ablation system that overcomes the shortcomings of these mono-polar tissue ablation devices.

Figure 1:
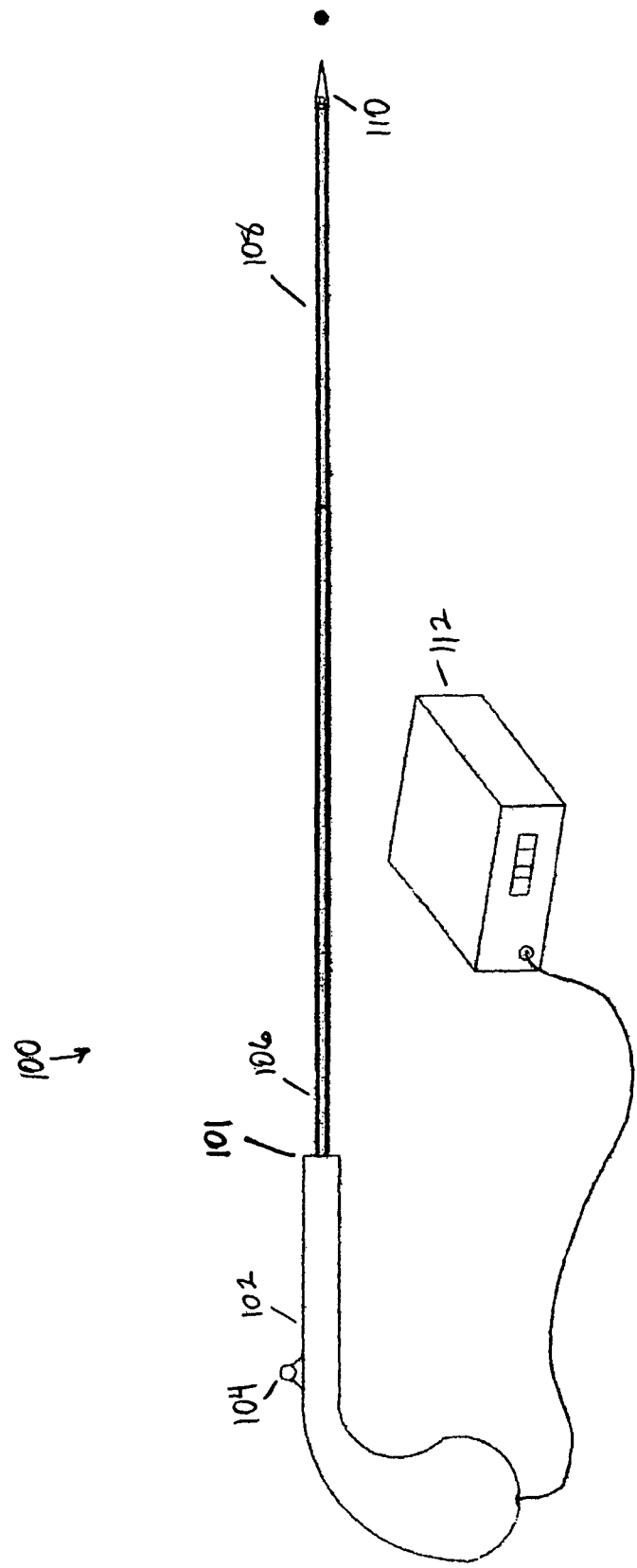
FIG. 1 is a tissue ablation device including a hand piece, a deployment slider, a delivery member/tube, and a plurality of energy conduits in a retracted state coupled among an energy source and a distal tip, under an embodiment.

In the drawings, the same reference numbers identify identical or substantially similar elements or acts. To easily identify the discussion of any particular element or act, the most significant digit or digits in a reference number refer to the Figure number in which that element is first introduced (e.g., element 108 is first introduced and discussed with respect to FIG. 1).

DETAILED DESCRIPTION

A tissue ablation system including numerous components and methods is described herein for encircling target tissue and generating tissue ablation volumes in various biological tissues. The biological tissue includes tissue of a variety of organs of the human body including the liver, spleen, kidney, lung, breast and other organs, but is not so limited. In the following description, numerous specific details are introduced to provide a thorough understanding of, and enabling description for, embodiments of the tissue ablation system. One skilled in the relevant art, however, will recognize that the tissue ablation system can be practiced without one or more of the specific details, or with other components, systems, etc. In other instances, well-known structures or operations are not shown, or are not described in detail, to avoid obscuring aspects of the tissue ablation system.

Figure 2:
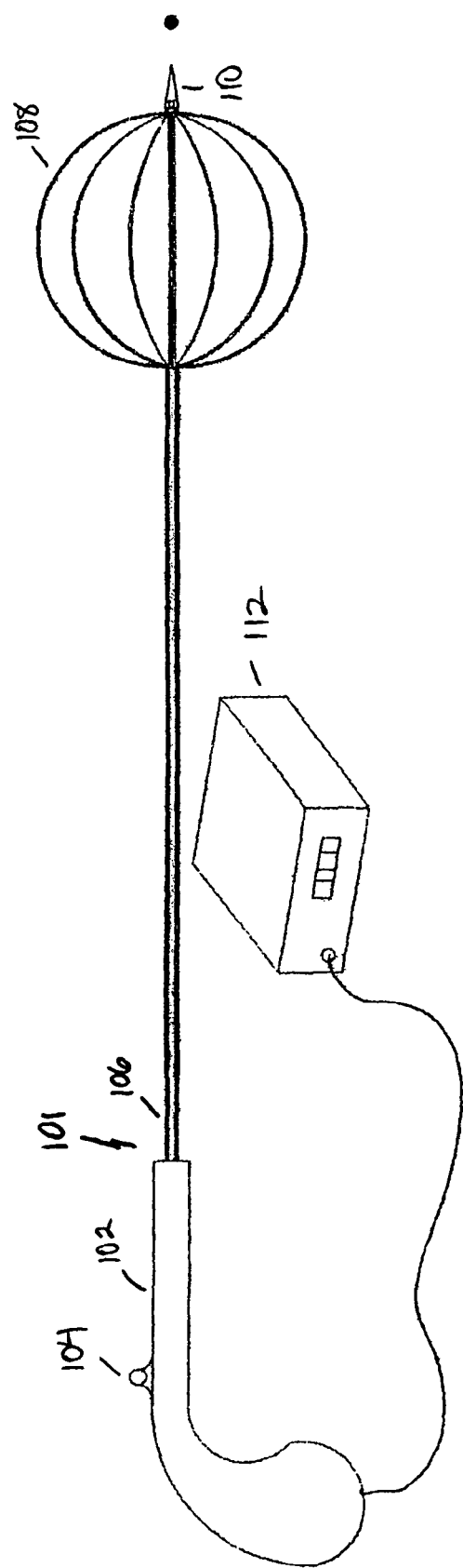
FIG. 2 is a tissue ablation device including a hand piece, a deployment slider, a delivery member/tube, and a plurality of energy conduits in a deployed state coupled among an energy source and a distal tip, under the embodiment of FIG. 1.

FIG. 1 is a tissue ablation system 100, under an embodiment. The tissue ablation system 100 includes a tissue ablation device 101 coupled to at least one energy source 112. The tissue ablation device 101 includes a hand piece 102, a deployment slider 104, a delivery member/tube 106, a plurality of energy conduits 108, and a distal tip 110, under an embodiment. The energy conduits 108, also referred to herein as electrodes 108, are in a retracted state, but are not so limited. FIG. 2 is a tissue ablation device with the energy conduits 108 in a deployed state, under an embodiment. The tissue ablation device 101 can also include other components as known in the art and as appropriate to procedures including the tissue ablation device 101.

The components of the tissue ablation system 100 are described in turn with reference to FIG. 1 and FIG. 2. The hand piece 102 of the tissue ablation device 101 includes a handle by which the user grips the tissue ablation device 101. The hand piece 102 provides a coupling between the energy source 112 and one or more of the energy conduits 108 which may or may not be coupled to at least one of the hand piece 102 and the energy source 112. The deployment slider 104 or advancement mechanism 104, which in an embodiment is integral to the hand piece 102, deploys or retracts the energy conduits 108 upon actuation.

The tissue ablation device 101 also includes a delivery member/tube 106 that supports placement of the energy conduits 108 in the target tissue, but is not so limited. The delivery member/tube 106 is formed using material that is at least one of electrically conductive, conditioned, and coated to allow for electrical conductivity via the electrodes. As an example, the delivery member/tube 106 is formed using at least one of stainless steel, nickel titanium, alloys, and plastics including Ultem, Polycarbonate, and Liquid crystal polymer, but is not so limited. The delivery member/tube 106 has a diameter approximately in a range of 0.05 to 0.5 inches, and has a length approximately in a range of 0.1 to twenty (20) inches as appropriate for extension into a body region appropriate to the treatment procedure. As one example, the delivery member/tube 106 of an embodiment has a diameter of between approximately 0.08 and 0.3 inches and a length between approximately two (2) and twelve (12) inches.

The energy conduits 108 while configured appropriately for insertion into particular tissue types, are formed from one or more materials and have a shape, size, and pattern that supports coupling to the target tissue and allows the energy conduits 108 to deliver sufficient energy to ablate the target tissue. The energy conduits 108 include materials selected from among conductive or plated metals and/or plastics, super alloys including shape memory alloys, and stainless steel, to name a few. The energy conduits 108 comprise nickel titanium alloy, for example, but can be formed from any number/combination of materials including stainless steel, nickel titanium, and various alloys.

The energy conduits 108 of an embodiment, which collectively may be referred to as an electrode array 108, can have many different sizes (including lengths and diameters) depending upon the energy delivery parameters (current, impedance, etc.) of the corresponding system. The use of energy conduits 108 having different diameters allows for balancing of energy/energy density in the target tissue. Therefore, the use of energy conduits 108 having different diameters provides a means of control over energy balancing in the target tissue in addition to the spacing between the energy conduits 108. An outside diameter of one or more of the energy conduits 108 of an embodiment is approximately in the range of 0.005 to 0.093 inches, but is not so limited. Further, the energy conduits 108 of an embodiment have lengths sufficient to generate or create an ablation diameter approximately in the range of one (1) to fifteen (15) centimeters (cm), but are not so limited. As one example, the energy conduits 108 of an embodiment have an outside diameter between approximately 0.01 and 0.025 inches and lengths sufficient to generate or create an ablation diameter approximately in the range of three (3) to nine (9) centimeters (cm).

The energy conduits 108 of various alternative embodiments can include materials that support bending and/or shaping of the energy conduits 108. Further, the energy conduits 108 of alternative embodiments can include non-conducting materials, coatings, and/or coverings in various segments and/or proportions along the shaft of the energy conduits 108 as appropriate to the energy delivery requirements of the corresponding procedure and/or the type of target tissue The energy source 112 of an embodiment (also referred to as a generator 112 or electrical generator 112) delivers pre-specified amounts of energy at selectable frequencies in order to ablate tissue, but is not so limited. The energy source 112 includes at least one of a variety of energy sources including electrical generators operating within the radio frequency (RF) range. More specifically, the energy source 112 includes an RF generator operating in a frequency range of approximately 375 to 650 kHz and at a current of approximately 0.1 to 5 Amps and an impedance of approximately 5 to 100 ohms, but is not so limited. As an example, the energy source 112 of an embodiment operates at a frequency approximately in the range of 400 kHz to 550 kHz and at a current of approximately 0.5 to four (4) Amps, but is not so limited. Variations in the choice of electrical output parameters from the energy source 112 to monitor or control the tissue ablation process may vary widely depending on tissue type, operator experience, technique, and/or preference.

The tissue ablation system 100 can include any number of additional components like, for example, a controller (not shown) to semi-automatically or automatically control delivery of energy from the energy source 112. The controller can, for example, increase the power output to the energy conduits 108, control temperature when the energy conduits 108 include temperature sensors or when receiving temperature information from remote sensors, and/or monitor or control impedance, power, current, voltage, and/or other output parameters. The functions of the controller can be integrated with those of the energy source 112, can be integrated with other components of the tissue ablation system 100, or can be in the form of stand-alone units coupled among components of the tissue ablation system 100, but are not so limited.

Moreover, the tissue ablation system 100 can include an operator display (not shown) that provides a display of heating parameters such as temperature for one or more of the energy conduits 108, impedance, power, current, timing information, and/or voltage of the energy source 112 output. The functions of the display can be integrated with those of the energy source 112, can be integrated with other components of the tissue ablation system 100, or can be in the form of stand-alone units coupled among components of the tissue ablation system 100, but are not so limited.

In operation, a user advances the deployment slider 104, and in response the energy conduits 108 are forced, or in the case of a pre-shaped energy conduits, released from the retracted state to the deployed state. The shape of the deployed energy conduits can, as shown in FIG. 2, form a series of approximately semi-spherical segments that, when taken together, form the outline of a sphere. The tissue ablation device generates a spherical volume of ablated tissue upon application of energy to the deployed electrodes.

Figure 3:
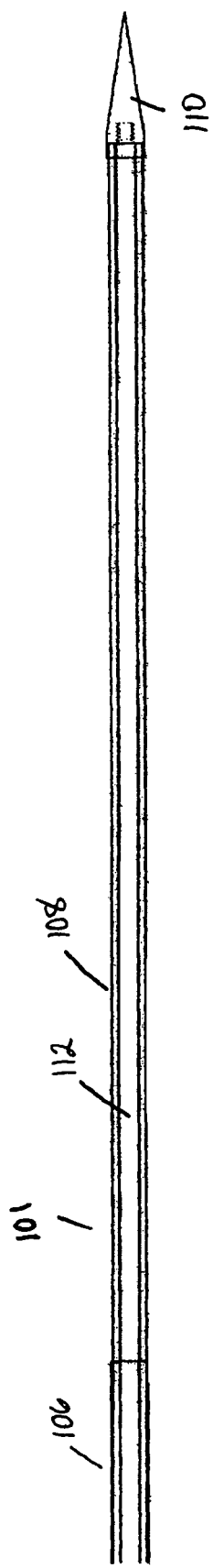
FIG. 3 is a distal portion of a tissue ablation device including a delivery member/tube and a plurality of energy conduits in a retracted state, under the embodiment of FIG. 1.

FIG. 3 is the distal portion of a tissue ablation device 101 including a delivery member/tube 106, a deployment member or rod 112, a plurality of energy conduits 108 in a retracted state (two energy conduits are shown for simplicity, but the embodiment is not so limited), and a distal tip 110, under the embodiment of FIG. 1. The energy conduits 108 are coupled, either individually or collectively, to an energy source or generator (not shown). When the energy conduits 108 are in the retracted state, the distal portion of the tissue ablation device presents a very streamline profile well suited to piercing tissue and advancement/placement in/near an area which might contain a malignant or non-malignant tumor. By piercing the tumor the distal tip can be placed just beyond the tumor.

Figure 4:
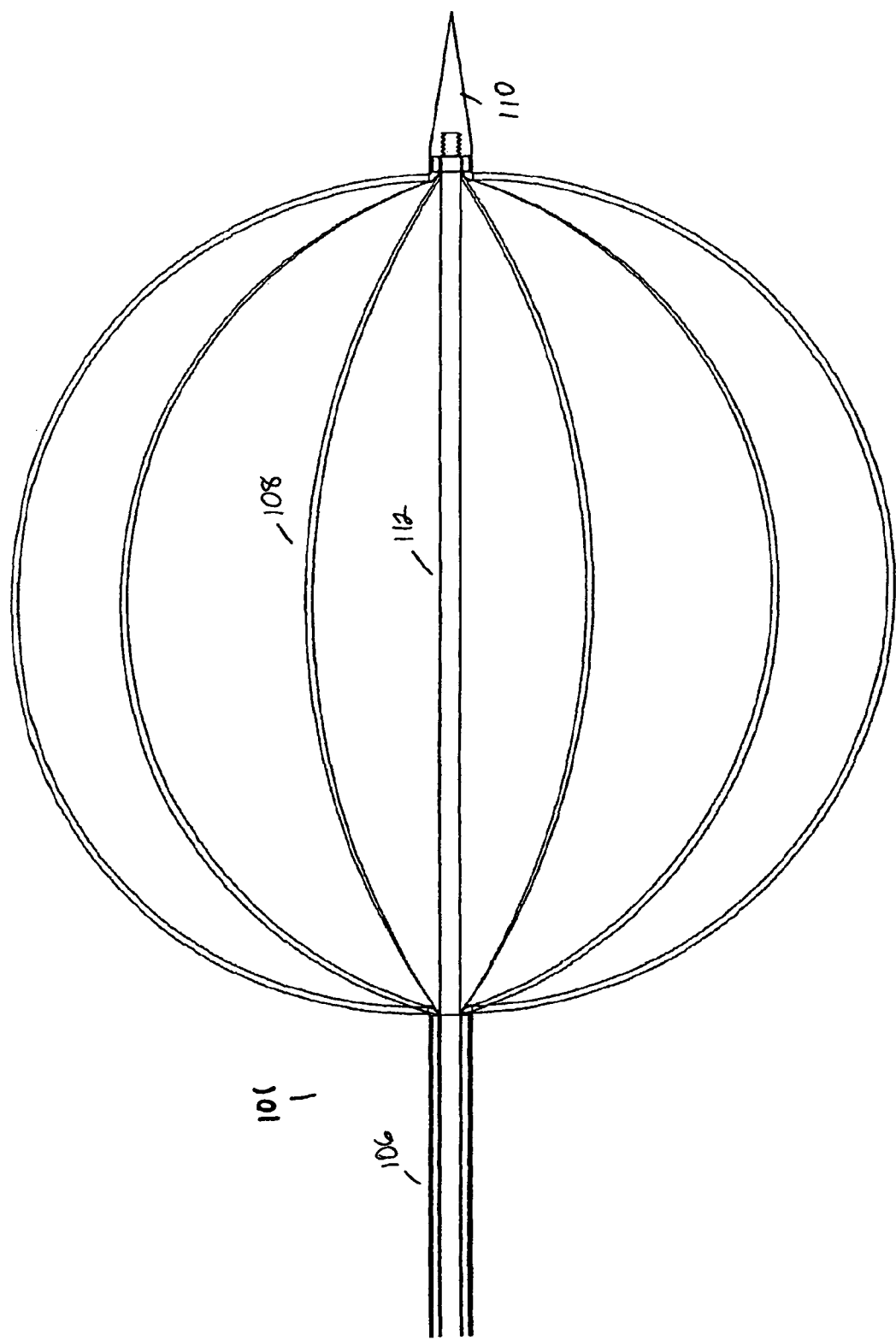
FIG. 4 is a distal portion of a tissue ablation device including a delivery member/tube and a plurality of energy conduits in a deployed state, under the embodiment of FIG. 1.

FIG. 4 is the distal portion of a tissue ablation device 101 including a delivery member/tube 106, a deployment member or rod 112, a plurality of energy conduits 108 in a deployed state, and a distal tip 110, under the embodiment of FIG. 1. The energy conduits 108 are coupled, either individually or collectively, to an energy source or generator (not shown). Following placement of the distal portion of the tissue ablation device in the target tissue as appropriate to the corresponding medical procedure, the user advances the deployment slider (not shown) to deploy the energy conduits 108, thus fully encompassing the volume of tissue desired to be ablated.

Regarding deploying of the energy conduits 108, some or all of the energy conduits 108 can be deployed in response to advancement of the deployment slider. For example, all energy conduits 108 of an embodiment are deployed simultaneously in response to advancement of the deployment slider. As another example, one set of energy conduits 108 can be deployed to form a sphere having a first diameter while another set of energy conduits 108 can be deployed to form a sphere having a second diameter. Other alternative embodiments can use additional deployment schemes known in the art.

The energy conduits 108 of an embodiment deliver radio frequency (RF) current to the target tissue and, as such, can be of alternating electrical polarity. The alternating polarity series of energy conduits includes various series combinations of alternating polarities. For example, in an embodiment using ten (10) energy conduits, the alternating polarity is: positive polarity (+), negative polarity (−), +, −, +, −, +, −, +, −. An alternative polarity series is: +, +, −, −, +, +, −, −, +, +. Another alternative polarity series is: −, −, +, +, −, −, +, +, −, −. Yet another alternative polarity series is: +, +, +, +, +, −, −, −, −, −. These examples are only illustrative of possible polarity configurations, and the tissue ablation system 100 described herein is not limited to ten (10) electrodes or to these alternating polarity configurations.

The energy conduits of an alternative embodiment conduct electricity of a single electrical polarity, while the deployment rod 112 conducts electricity having an opposite polarity to that of the energy conduits. In still another alternative embodiment, the deployable energy conduits are switched between the same electrical polarity with the deployment rod being the other and alternating polarity between the deployable energy conduits. In yet another alternative embodiment, the deployment rod and deployable energy conduits are of a single electrical polarity and one or more secondary grounding pads are used therewith to provide an opposite polarity member.

Various alternative embodiments can simultaneously use any number of energy conduits in a procedure in order to form volumes of ablated tissue having shapes and sizes appropriate to the treatment procedure. Numerous alternatives would be recognized by those skilled in the art in view of the tissue ablation device described herein.

Figure 5:
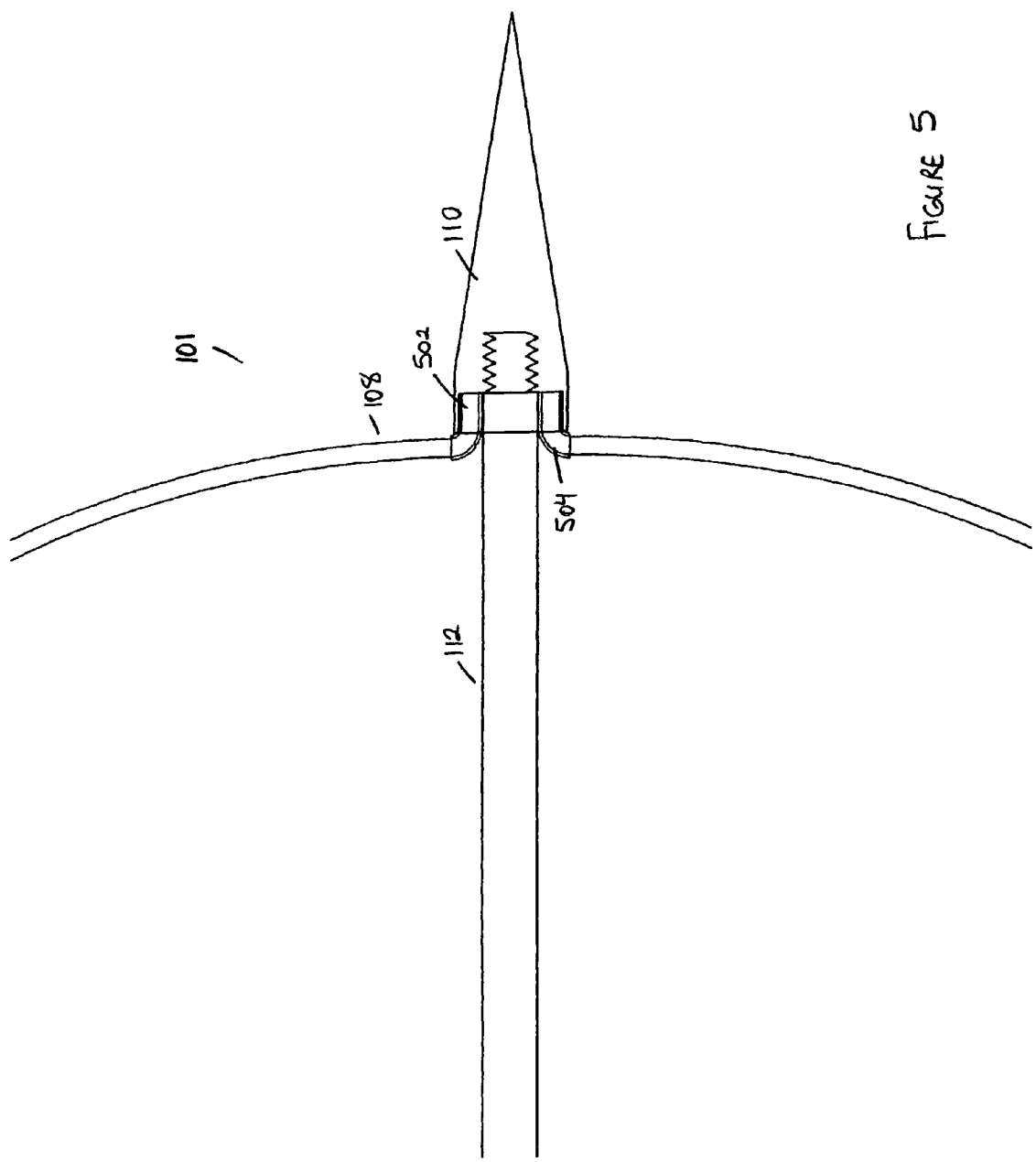
FIG. 5 shows an enlarged view of the distal portion of a tissue ablation device including a center deployment rod and a plurality of energy conduits in a deployed state, under the embodiment of FIG. 1.

FIG. 5 shows a distal region or portion of a tissue ablation device 101 including a center deployment rod 112, a plurality of energy conduits 108 in a deployed state (two energy conduits are shown for simplicity, but the embodiment is not so limited), conduit insulators 504, and a distal tip 110, under the embodiment of FIG. 1. In support of delivering electrical energy of alternating polarity via the energy conduits 108, the conduit insulators 504 mechanically couple the distal ends of the energy conduits 108 while maintaining electrical insulation between each of the energy conduits 108. In this tissue ablation device the deployable energy conduits 108 are coupled to the conduit insulators 504. The combination of the energy conduits 108 and the conduit insulators 504 is coupled to a non-electrically conductive retaining disk 502 that is coupled to an electrically conductive deployment member 112. Also connected to the deployment member 112 is the electrically conductive distal tip 110 that, in this embodiment, is suitable for piercing tissue. Advancing the deployment slider causes the deployable energy conduits or electrodes 108 to experience a compressive load. As this force increases beyond the column strength of the deployable energy conduits 108, the energy conduits 108 buckle and deploy outward in a controlled fashion.

Alternatively, the energy conduits 108 can be pre-formed to a desirable shape when fabricated of a suitable material such as a nickel titanium (NiTi) alloy. Using the pre-formed electrodes, advancement of the deployment slider permits the deployable electrodes to return to their preformed shape. The application of a small amount of energy such as RF current can help to facilitate the deployment of the electrodes through the tissue.

Figure 6:
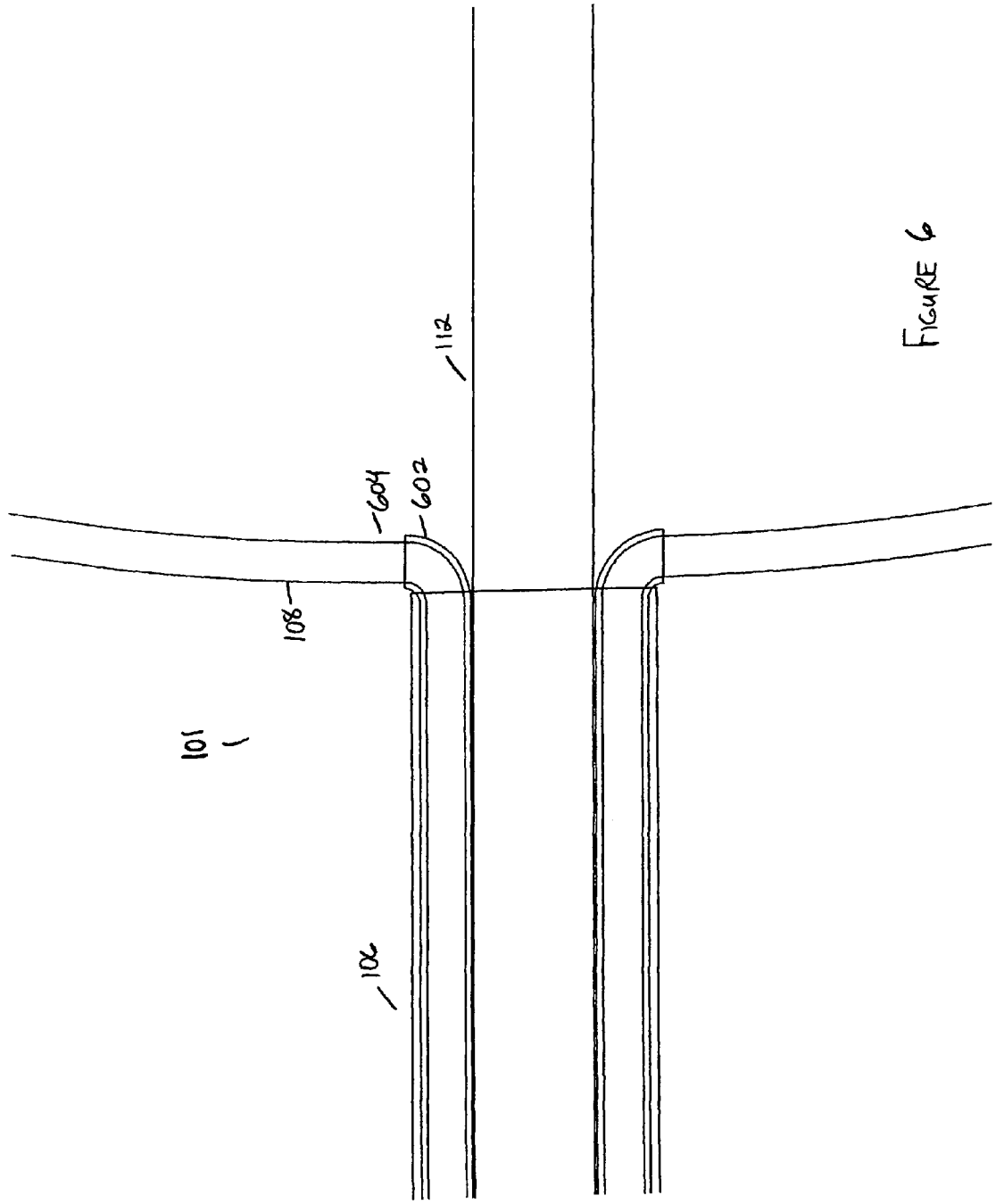
FIG. 6 shows an enlarged view of the mid-section of a tissue ablation device including a center deployment rod and a plurality of energy conduits in a deployed state, under the embodiment of FIG. 1.

FIG. 6 shows a mid-section of a tissue ablation device 101 including a delivery member/tube 106, a deployment member 112, and a plurality of energy conduits 108 in a deployed state (two energy conduits are shown for simplicity, but the embodiment is not so limited), under the embodiment of FIG.

1. The proximal end 604 of the energy conduits 108 couples to an electrical insulator 602 or insulating material 602, but is not so limited.

Figure 7:
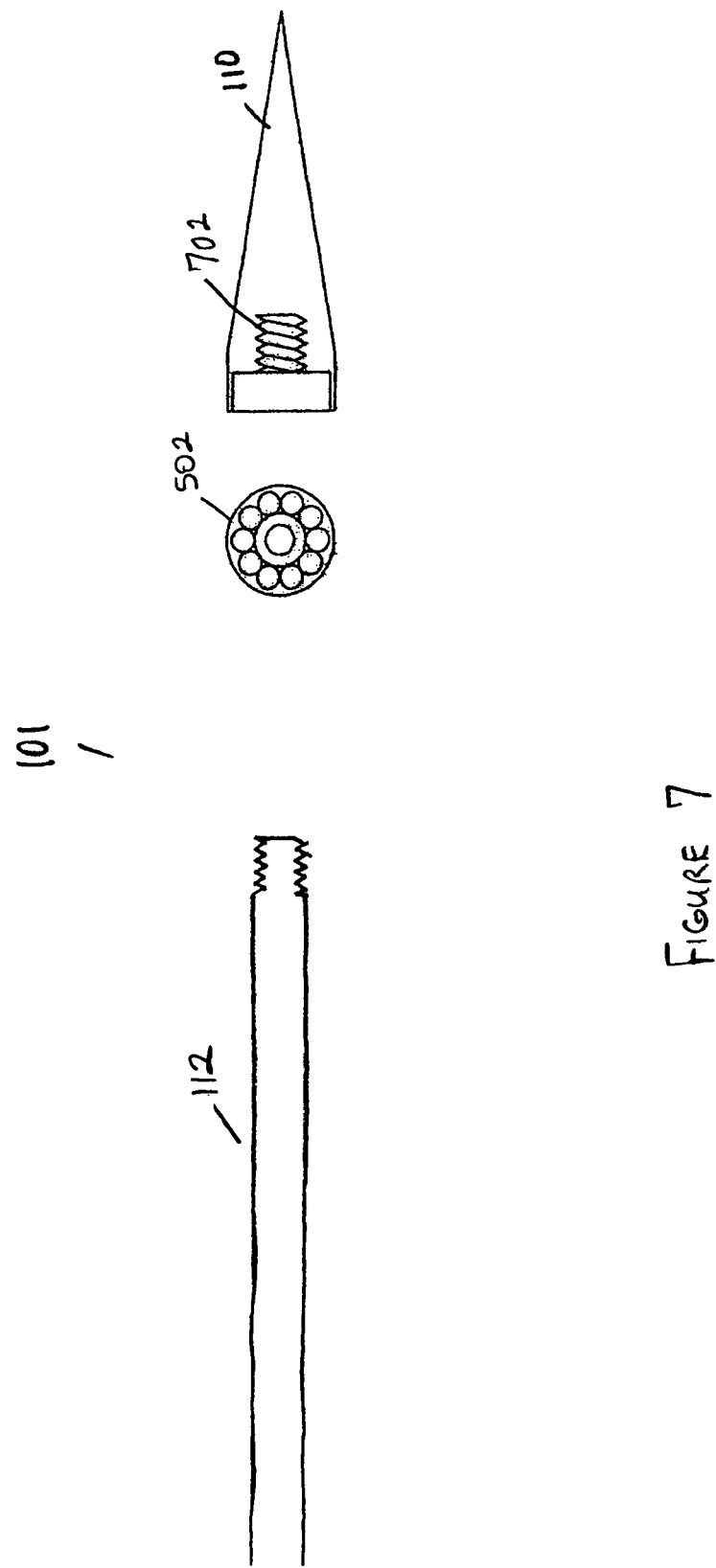
FIG. 7 shows an exploded view of the distal end of a tissue ablation device including a center deployment rod along with a rotated side view of the delivery member/tube including a plurality of energy conduits and deployment rod, and a distal tip, under the embodiment of FIG. 1.

FIG. 7 shows an exploded view of a distal region of a tissue ablation device 101 including a deployment member 112, a distal tip 110, and a rotated side view of an energy conduit retaining disk 502, under the embodiment of FIG. 1. Although a variety of methods exists to couple the components of the tissue ablation device 101 at the distal end, one such method is a simple screw thread 702 configured to accept a distal end of the deployment member 112. Alternatively, a press or interference fit between mating parts or the use of various adhesives can also be used. The retaining disk 502, as described above with reference to FIG. 5, is configured couple to the deployment member 112 and the distal tip 110.

Figure 8:
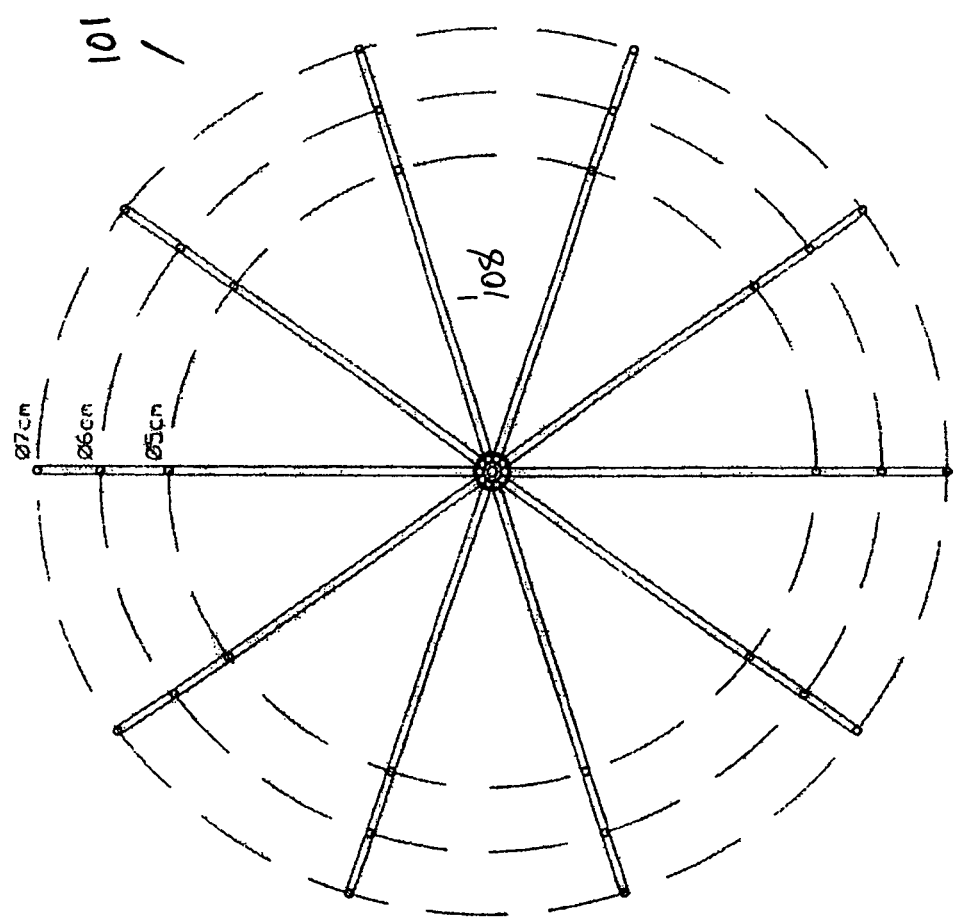
FIG. 8 is an end view of a plurality of deployed energy conduits having diameters of 5, 6, and 7 centimeters (cm), under the embodiment of FIG. 1.

FIG. 8 is an end view of a tissue ablation device 101 with deployed energy conduits 108 forming spheres having diameters of approximately 5, 6, and 7 centimeters (cm), under the embodiment of FIG. 1. The tissue ablation device 101 of an embodiment provides approximately uniform spacing among the energy conduits 108, but alternative embodiments may support any number/combination of energy conduit 108 configurations. The tissue ablation device 101 of an embodiment supports a variety of spherical deployment sizes by providing control over the extent to which the deployable energy conduits are deployed via the deployment slider, but is not so limited.

Figure 9:
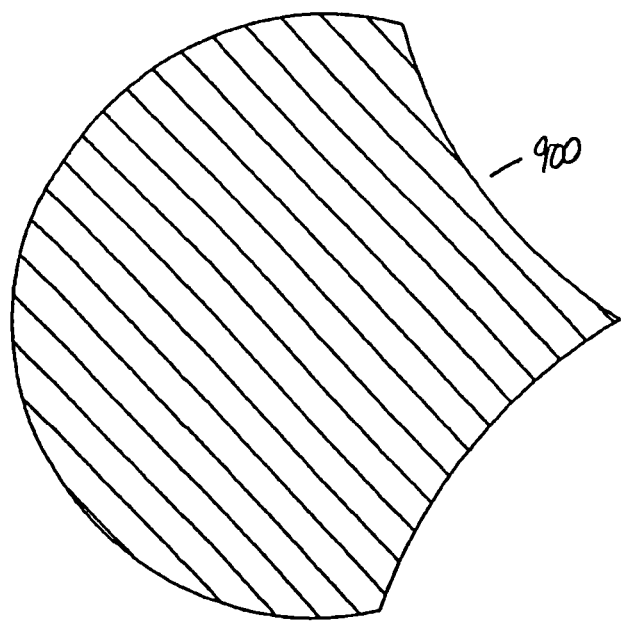
FIG. 9 is a cross-section of an energy conduit configured for at least one of cutting, separating, and parting tissue as it is pressed or forced against the tissue, under an embodiment.

FIG. 9 is a cross-section of an energy conduit 900 configured for at least one of cutting, separating, and parting tissue as it is pressed or forced against the tissue, under an embodiment. The energy conduit 900 is used to form the energy conduits 108 described above with reference to FIG. 1. As the energy conduits 900 are advanced from the retracted state (FIG. 3) to the deployed or expanded state (FIG. 4), the energy conduits 900 penetrate or separate the surrounding tissue. This penetration is accomplished in one embodiment using energy conduits that have a geometry suited for separating or cutting the surrounding tissue. The penetration of tissue by the energy conduits 900 in an alternative embodiment is accomplished with the application of energy, for example RF energy, to the energy conduit 900 in order to facilitate cutting through the tissue during advancement of the energy conduits. Another alternative embodiment includes the use of both an energy conduit 900 having a cutting geometry along with the application of a suitable electrical energy to the energy conduit 900.

Figure 10:
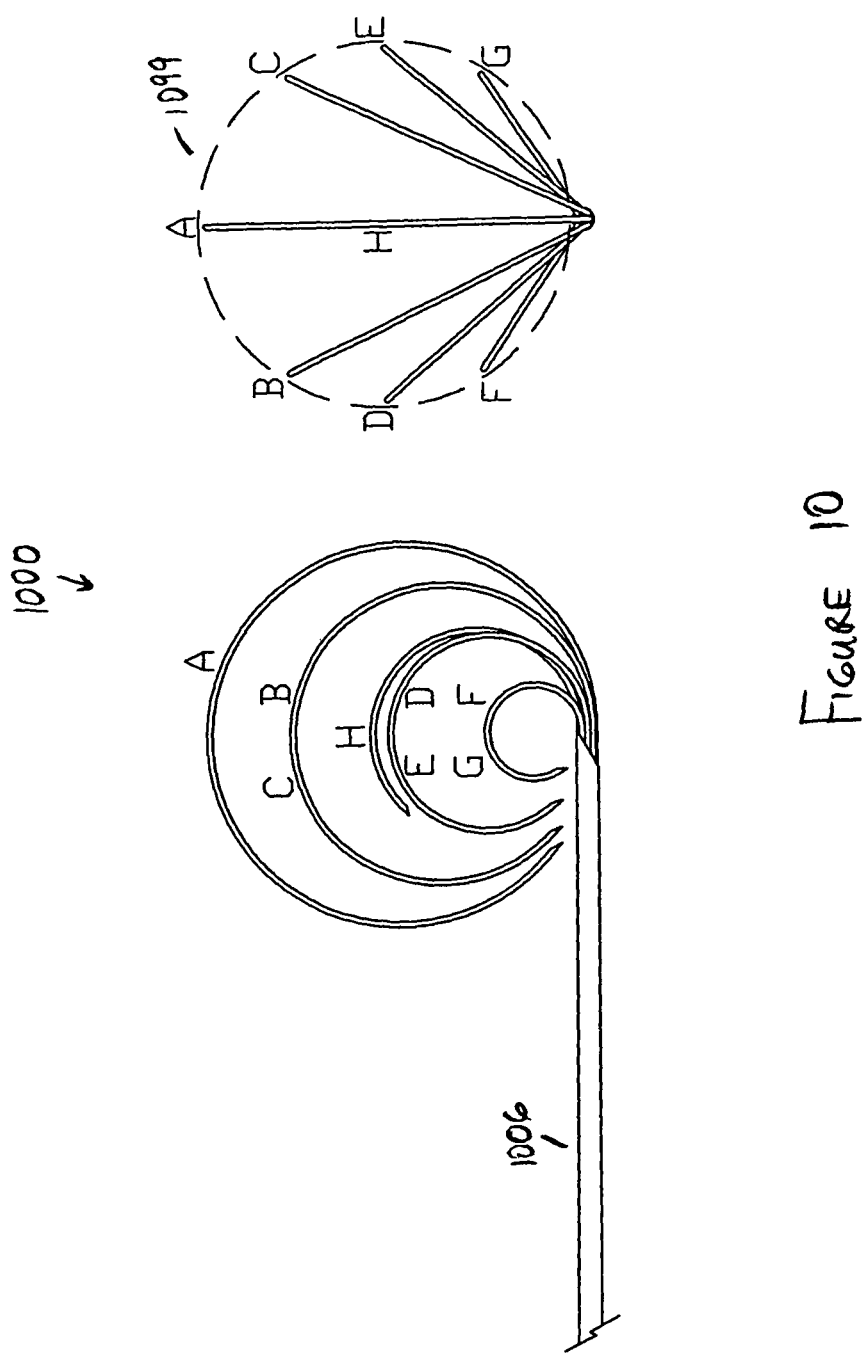
FIG. 10 is a distal portion of a tissue ablation device including a delivery member/tube and a plurality of energy conduits in a deployed state, under an alternative embodiment.

FIG. 10 is a distal portion 1000 of a tissue ablation device including a delivery member/tube and a plurality of energy conduits A, B, C, D, E, F, and G (collectively referred to as A-G) in a deployed state, under an alternative embodiment. The energy conduits A-G comprise nickel titanium alloy, for example, but can be formed from any number/combination of materials. Further, the outside diameter of the energy conduits A-G of an embodiment is approximately in the range of 0.010 to 0.040 inches, but is not so limited.

As described above, the delivery member/tube 1006 provides sufficient support for placement of the energy conduits A-G. Advancement of a deployment slider (not shown) advances and deploys the energy conduits A-G to a deployed shape. The shape of these energy conduits A-G can form a series of approximately semi-spherical segments which in this embodiment when taken together form the outline of a sphere 1099 that fully encompasses a volume of tissue targeted for ablation. The application of RF energy to the energy conduits A-G generates or produces a spherical volume of ablated tissue.

The energy conduits A-G of an embodiment are configured to each have an alternating electrical polarity. The energy conduits of an alternative embodiment are of a single electrical polarity, with the delivery member/tube 1006 conducting an opposite polarity. In still another alternative embodiment, the energy conduits A-G are individually switched between the same electrical polarity and the delivery member/tube 1006 conducts an opposite/alternating polarity to that of the energy conduits A-G. In yet another alternative embodiment, the delivery member/tube 1006 and energy conduits A-G are of a single electrical polarity and one or more secondary grounding pads are used therewith to provide an opposite polarity member.

In operation, the tissue ablation system of an embodiment delivers energy to target tissue via the energy conduits A-G. The energy includes, for example, radio frequency (RF) energy, but is not so limited. The energy is delivered via any of a number of techniques. The energy can be applied via pulsed waveforms and/or continuous waveforms, but is not so limited.

In an example procedure that includes use of the tissue ablation system, energy can be applied to energy conduits A-G during deployment of the energy conduits A-G into the target tissue. The energy can be applied automatically or, alternatively, manually as a procedure progresses and as appropriate to the procedure. Also, the energy delivered to the target tissue can be adjusted during the procedure by adjusting any of the power level, the waveforms, and a combination of the power level and the waveform.

In another example procedure that includes use of the tissue ablation system, energy can be applied to energy conduits A-G following deployment of the energy conduits A-G into the target tissue. The energy can be applied automatically or, alternatively, manually as appropriate to the procedure. Also, the energy delivered to the target tissue can be adjusted manually and/or automatically during the procedure by adjusting any of the power level, the waveforms, and a combination of the power level and the waveform.

In addition to the components of the tissue ablation device 1000, various sensing techniques can be used to guide or control the progress of the tissue ablation. For example temperature sensors can be embedded or attached to at least one of the energy conduits A-G and the delivery member/tube 1006 to provide feedback to a user and/or an energy controller. Additionally, a variety of sensors can be deployed from the tissue ablation device 1000 into tissue of the target tissue.

In addition to the components of the tissue ablation systems described above, various sensing techniques can be used with and/or coupled to the tissue ablation system to guide or control the progress of the tissue ablation. For example temperature sensors can be embedded or attached to the deployable energy conduits and provide feedback to a user or an energy controller. A variety of sensors can also be deployed from the device into tissue within the targeted tissue, in this case a sphere.

Figure 11:
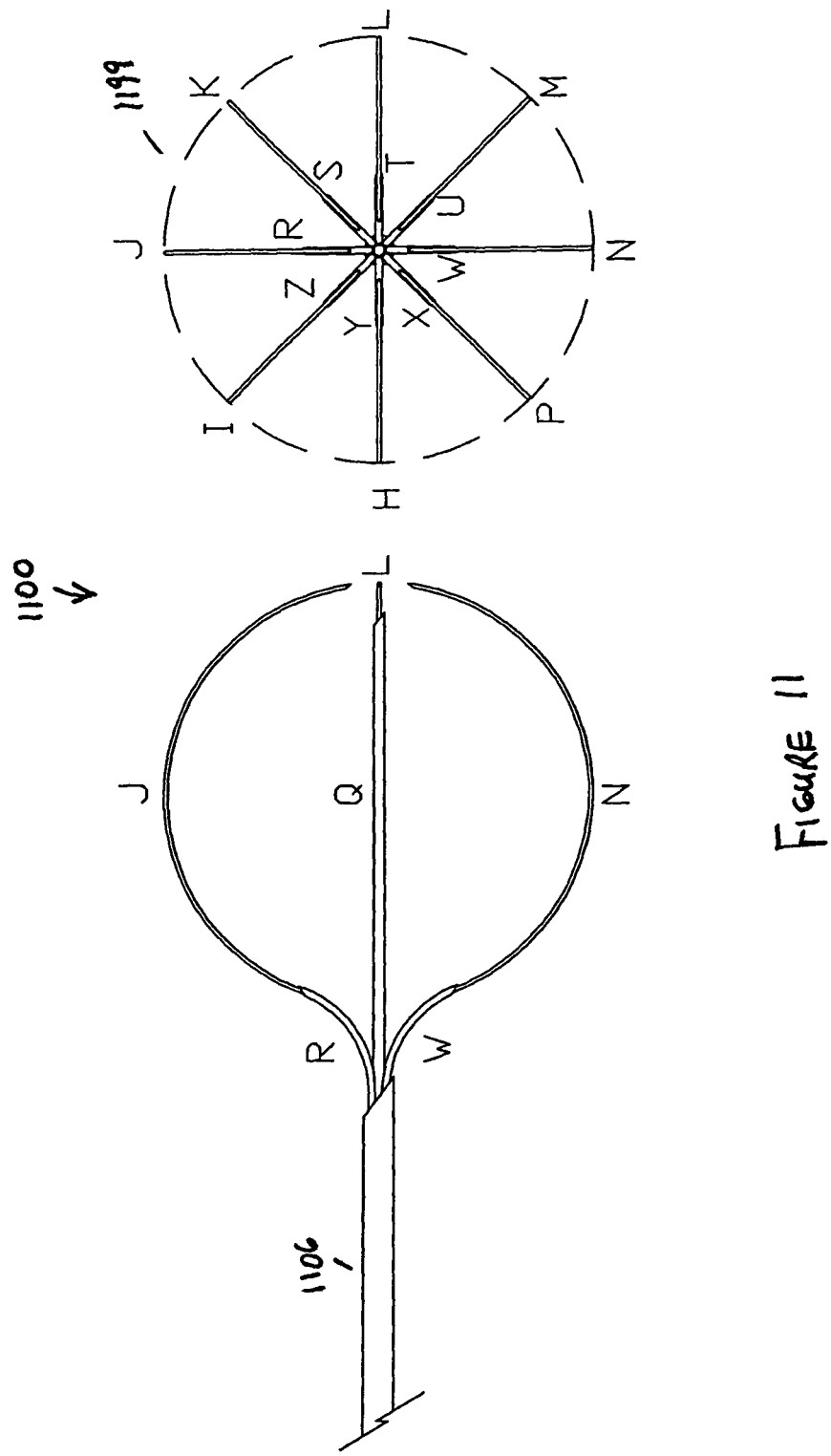
FIG. 11 is a distal portion of a tissue ablation device including a delivery member/tube and a plurality of energy conduits in a deployed state, under yet another alternative embodiment.

FIG. 11 is a distal portion 1100 of a tissue ablation device including a delivery member/tube 1106, a plurality of primary energy conduits R, S, T, U, W, X, Y, Z (collectively referred to as R-Z), and a plurality of secondary energy conduits H, I, J, K, L, M, N, and P (collectively referred to as H-P) and Q in a deployed state, under yet another alternative embodiment. For clarity electrodes H, I, K, M, P, S, T, U, X, Y, and Z have been omitted in the side view of the device shown in FIG. 11. The primary R-Z and secondary H-P energy conduits comprise nickel titanium alloy, for example, but can be formed from any number/combination of materials some of which are described above. Further, the outside diameter of the primary R-Z and secondary H-P energy conduits of an embodiment is approximately in the range of 0.010 to 0.080 inches, but is not so limited.

As described above, the delivery member/tube 1106 provides sufficient support for placement of the primary energy conduits R-Z. Likewise the primary energy conduits R-Z provide sufficient support for placement of the secondary energy conduits H-P. While the tissue ablation device of an embodiment deploys one secondary energy conduit from one or more distal and/or lateral ports in a distal region of each primary energy conduit, alternative embodiments of the tissue ablation device can deploy more than one secondary energy conduit from one or more distal and/or lateral ports of each primary energy conduit. Advancement of a deployment slider (not shown) as described above advances and deploys the energy conduits R-Z, H-P, and Q to a deployed state or shape in target tissue. The energy conduits R-Z, H-P in a deployed state form a series of approximately semi-spherical segments which when taken together in this embodiment form the outline of a sphere 1199 that fully encompasses a volume of tissue targeted for ablation. The application of RF energy to the energy conduits R-Z, H-P, and Q generates or produces a spherical volume of ablated tissue.

The energy conduits R-Z, H-P, and Q of an embodiment are configured to each have an alternating electrical polarity. The energy conduits of an alternative embodiment conduct electrical energy of a single electrical polarity, with the delivery member/tube 1106 conducting electrical energy having an opposite polarity. In still another alternative embodiment, the energy conduits H-P and R-Z are individually switched between the same electrical polarity and electrode Q is coupled to conduct electrical energy of an opposite/alternating polarity to that of the energy conduits H-P and R-Z. In yet another alternative embodiment, all energy conduits R-Z, H-P, and Q are of a single electrical polarity and one or more secondary grounding pads are used therewith to provide an opposite polarity member. In still another embodiment, electrode Q is not present and energy passes within the remaining electrodes.

In operation, the tissue ablation system of an embodiment delivers energy to target tissue via the energy conduits R-Z, H-P, and Q. The energy includes, for example, radio frequency (RF) energy, but is not so limited. The energy is delivered via any of a number of techniques, some of which are described herein. The energy can be applied via pulsed waveforms and/or continuous waveforms, but is not so limited.

In an example procedure that includes use of the tissue ablation system, energy can be applied to energy conduits R-Z, H-P, and Q during deployment of the energy conduits R-Z, H-P, and Q into the target tissue. The energy can be applied automatically or, alternatively, manually as a procedure progresses and as appropriate to the procedure. Also, the energy delivered to the target tissue can be adjusted during the procedure by adjusting any of the power level, the waveforms, and a combination of the power level and the waveform.

In another example procedure that includes use of the tissue ablation system, energy can be applied to energy conduits R-Z, H-P, and Q following deployment of the energy conduits R-Z, H-P, and Q into the target tissue. The energy can be applied automatically or, alternatively, manually as appropriate to the procedure. Also, the energy delivered to the target tissue can be adjusted manually and/or automatically during the procedure by adjusting any of the power level, the waveforms, and a combination of the power level and the waveform.

In addition to the components of the tissue ablation device 1100, various sensing techniques can be used to guide or control the progress of the tissue ablation. For example temperature sensors can be embedded or attached to at least one of the energy conduits R-Z, H-P, and Q and the delivery member/tube 1106 to provide feedback to a user and/or an energy controller. Additionally, a variety of sensors can be deployed from the tissue ablation device 1100 into tissue of the target tissue.

In addition to the components of the tissue ablation systems described above, various sensing techniques can be used with and/or coupled to the tissue ablation system to guide or control the progress of the tissue ablation. For example temperature sensors can be embedded or attached to the deployable energy conduits and provide feedback to a user or an energy controller. A variety of sensors can also be deployed from the device into tissue within the targeted tissue, in this case a sphere.

Figure 12:
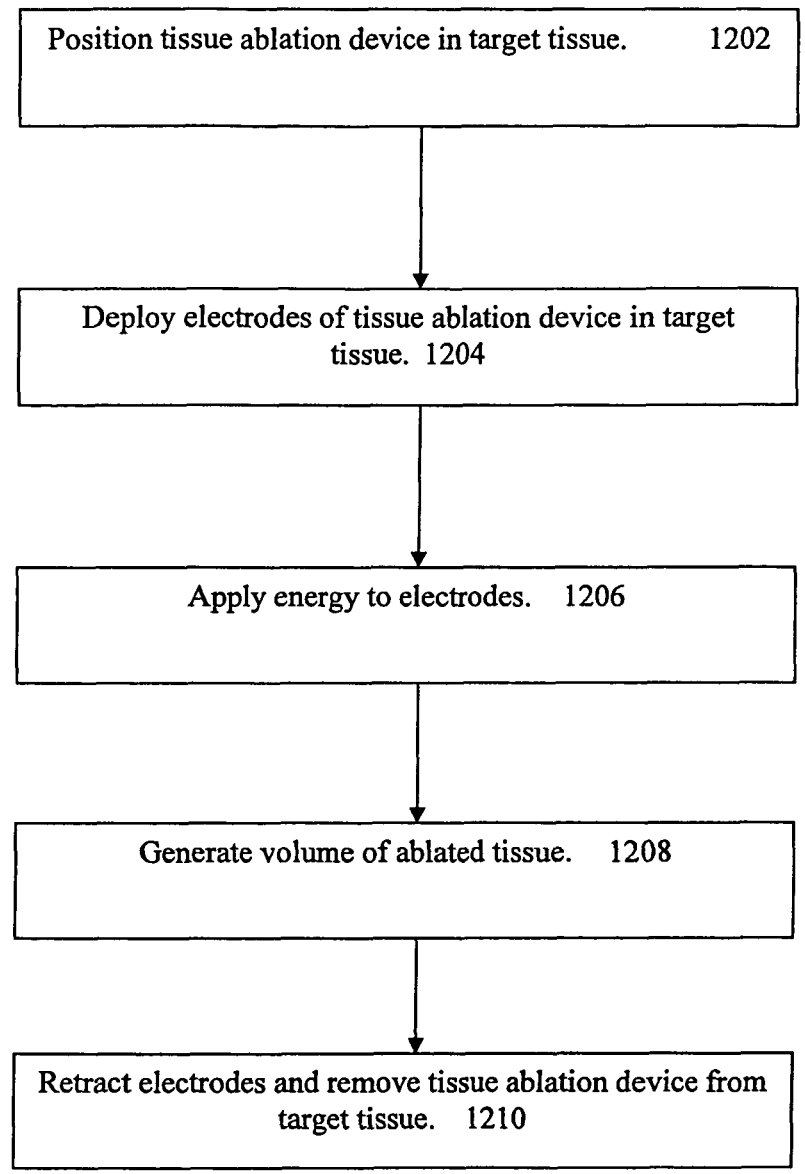
FIG. 12 is a flow diagram of tissue ablation procedure using the tissue ablation device, under an embodiment.

FIG. 12 is a flow diagram of tissue ablation procedure using the tissue ablation device, under an embodiment. In operation, generally a user positions the tissue ablation device in the target biological tissue as appropriate to a medical procedure, at block 1202. Placement of the tissue ablation device in the target tissue can include the use of various visualization methods such as ultrasound stenography, Computerized Tomography (CT), and Magnetic Resonance Imaging (MRI), but is not so limited.

Following placement of the device in the target tissue the user deploys the electrodes in the target tissue, at block 1204. Power or energy is applied to the target tissue via the electrodes, at block 1206. The energy generates a volume of ablated tissue having a shape and size appropriate to the configuration of the deployed electrodes, at block 1208. The user retracts the electrodes and removes the device from the target tissue, at block 1210.

In one or more additional embodiments, the electrodes of the ablation device can be configured to at least partially encircle the target tissue depending upon the location and distribution of the target tissue to be ablated. For these embodiment, one or more mono-polar or bipolar electrodes can be configured to totally surround or partially encircle the target tissue, e.g., a tumor, and application of energy through the electrodes is directed to create a spherical or relatively spherical area of ablation around and including the target tissue. Such a relatively spherical area could comprise an elongated spherical area (e.g., lozenge-shaped). The ablation area could also comprise an enclosed compound curved surface. One or more ablation devices, each containing an array of one or more electrodes is used to surround at least a portion of the target tissue or ablation volume and thereby ablate that portion upon deployment of the electrodes and application of energy from the energy source. Each such device thus creates an ablation pattern along one or more planes of the target tissue or ablation volume, and may be referred to as a "planar" device or electrode assembly.

Figure 13:
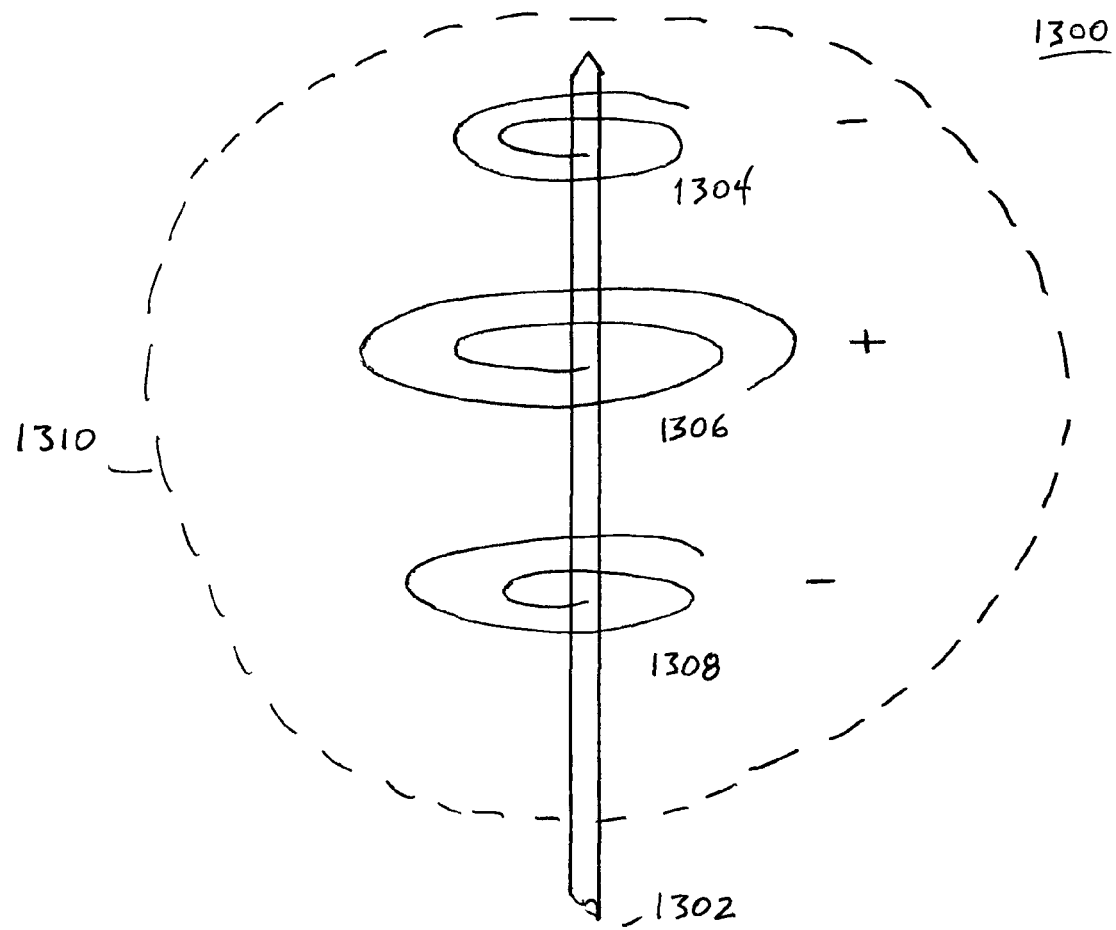
FIG. 13 illustrates a spiral electrode ablation device, according to an embodiment.

FIG. 13 illustrates a spiral electrode ablation device, according to an embodiment. Device 1300 comprises a trocar 1302, or similar penetrating device (also referred to as an "introducer" or "deliver member"). In general, the trocar is a sharply pointed shaft with a three-sided point and may be used within a cannula for insertion into body tissue; however, trocar 1302 may represent any suitable introducer or penetrating device that can house one or more electrode elements. A first electrode 1304 protrudes from the distal end of the trocar 1302 in a spiral configuration and in a plane perpendicular to the longitudinal axis of trocar 1302. A second electrode 1308 protrudes from the body of trocar 1302, also in a spiral configuration and parallel to electrode 1304. A third electrode 1306 is positioned in between the first and second electrodes 1304 and 1308, and protrudes in a spiral configuration parallel to these electrodes. The diameter of electrode 1306 is greater than that of electrodes 1304 and 1308 so that the ablation pattern on the target tissue 1310 is spherical or nearly spherical. By altering the relative sizes of electrodes 1304, 1306 and 1308, and their relative positions on the trocar, ablation patterns of various shapes and sizes can be produced. In general, electrodes 1304 and 1308 are the same diameter, and electrode 1306 is greater than both end electrodes. The spacing between the electrodes can be equidistant, or there can be an offset so that electrode 1306 is closer to one end electrode or the other. The electrodes 1304, 1306, and 1308 can be energized to specific polarities relative to one another. In one embodiment, the end electrodes 1304 and 1308 can be negatively charged, while the middle electrode 1306 is positively charged, or vice-versa.

The trocar 1302 is configured and used to initially locate the target tissue site 1310, and is coupled to an energy source, such as an RF generator of a suitable frequency to ablate the target tissue through the electrodes. Device 1300 can be used as a mono-polar or bi-polar device by including a dispersive pad. A thermosensor can be included in one or more of the electrodes for feedback or control, and impedance sensing can also be included for this purpose. One or more of the electrodes 1304, 1306, and 1308 can be made of a conductive material, such as stainless steel, NiTi, and so on, and can be shaped in the form of a round-section wire, flat wire, round tube, or flat tube, and so on. For the embodiment illustrated in FIG. 13, a three-electrode configuration is shown. Alternatively, only two electrodes may be used, of the same or different polarities, to create an ablation pattern around the target tissue 1310 that is not exactly spherical, or more than three electrodes may be used in different polarity configurations to further modify or define the ablation pattern. The electrodes as shown in FIG. 13 are disposed in a plane perpendicular to the axis of trocar 1302, however one or more of the electrodes may be biased at an angle relative to this axis to further modify or define the ablation pattern. Furthermore, the number of coils making up each of the electrodes can be altered to accommodate different energy sources and target tissue requirements.

In a further alternative embodiment of the device illustrated in FIG. 13, one or more of the spiral electrodes may be configured to deploy along the body of trocar 1302 by spiraling around the trocar in a direction parallel to the longitudinal axis of the trocar.

Figure 14:
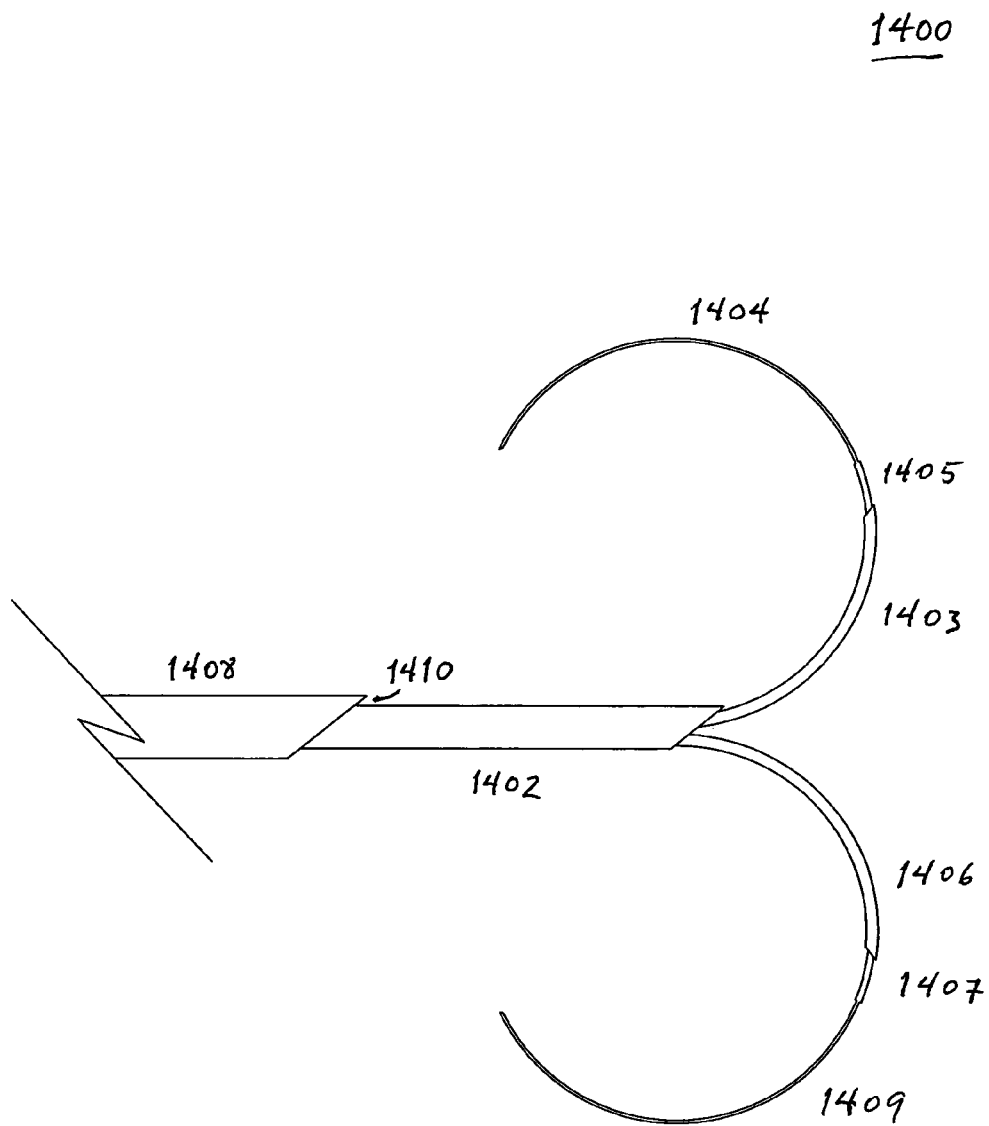
FIG. 14 illustrates a compound electrode ablation device including a fluid path, according to an embodiment.

The configuration and composition of an ablation device that is configured to encircle or at least partially encircle the target area can be implemented through various embodiments. FIG. 14 illustrates a compound electrode ablation device including a fluid path, according to an embodiment. For device 1400, two or more separate electrodes are deployed out of the distal end of trocar 1402. Each electrode comprises a compound electrode that has a positively charged portion and a negatively charged portion coupled together through an insulative member. Thus, FIG. 14 illustrates a device in which a first electrode includes a first portion 1403 and a second portion 1404 with an insulation member 1405, and a second electrode includes a first portion 1406 and a second portion 1409 with an insulation member 1407. The first portions 1403 and 1406 can be energized to a first polarity (e.g., negative), while the second portion of the electrodes can be energized to the opposite polarity (e.g., positive). The second portion of the electrode (e.g., 1404) can be installed and deployed through a lumen in the first portion of the electrode (e.g., 1403) around which an insulative sleeve (e.g., 1405) is inserted to maintain electrical isolation yet allow physical support of the second electrode portion within the first electrode portion.

Although two bipolar electrodes are illustrated in FIG. 14, it should be noted that a plurality of such compound electrodes can be deployed from trocar 1402, or they can be substituted by multiple single polarity electrodes. Furthermore, an additional electrode can be coupled to the body of the trocar itself. For the embodiment illustrated in FIG. 14, electrode 1408 is coupled to the body of trocar 1402 and electrically separated from electrodes 1404 and 1406 and 1402. A fluid path 1410 is formed between trocar 1402 and electrode 1408 to deliver fluid such as conductive saline. A dispersive electrode can be included in the device 1400 to create a mono-polar device, or a mono-polar/bi-polar device.

In one embodiment, an ablation device can formed by defining one of the electrodes as part of the trocar body and energizing this electrode with a polarity opposite that to one or more electrodes that are configured to protrude from an end or a portion of the trocar body. This creates an ablation pattern in a tissue field around the trocar when the protruding electrodes are deployed and energized relative to the electrode formed in the trocar body. Thus, with reference to the embodiment of FIG. 14, if electrode 1408 has a negative polarity and one or both of electrodes 1404 and 1406 and 1402 has a positive polarity, the deployment and energizing of the electrodes will cause ablation in a field surrounding the electrodes. The shape and size of the field can be defined by altering the number, length or size, and configuration of the electrodes, as well as the type and power of the energy source. For the embodiment illustrated in FIG. 14, in which the electrodes 1403/1404 and 1406/1409 are themselves compound electrodes, a separate electrode (e.g., electrode 1408) of a specific polarity may not necessarily need to be provided to form a bi-polar device. Furthermore, the coupling between the electrode 1408 may be through conductive fluid 1410, as shown, or it may be through an integrally-formed or adhesive-based coupling utilizing a second insulative member (not shown) to maintain electrical isolation between this electrode and the trocar body 1402.

To produce an electrode that is capable of having two or more polarities in a single element, the protruding electrodes shown in either FIG. 13 or FIG. 14 can be made out of a flat base material, such as a spring/sheet metal. A conductive coating can be applied to the base material through an insulative layer so that a single electrode can be configured to have two different polarities when energized.

Figure 15A:
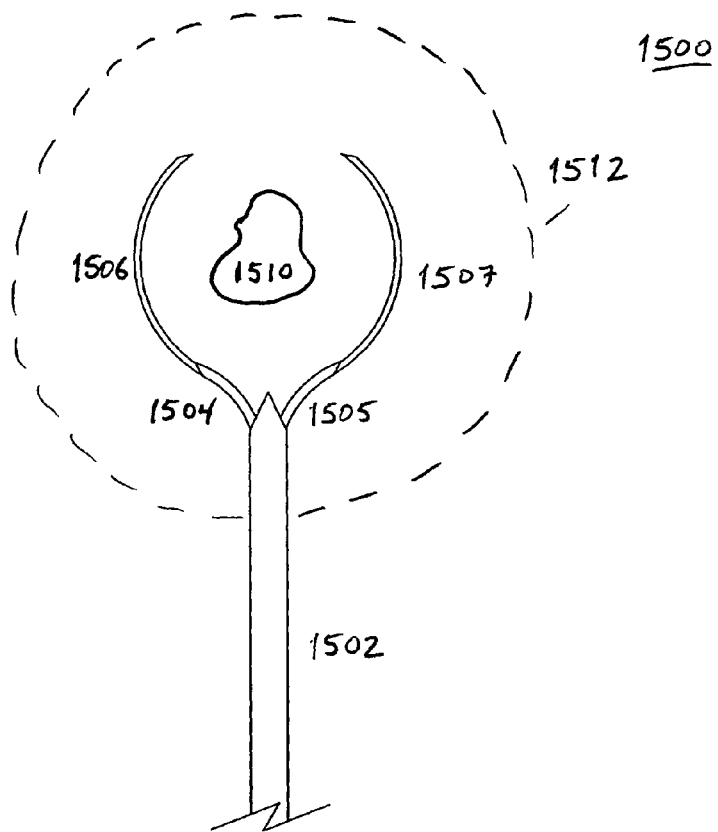
FIG. 15A illustrates a two stage ablation device for surrounding a target site, under an embodiment.

FIG. 15A illustrates a two-stage ablation device for surrounding a target site, under an embodiment. Device 1500 includes a set of electrode arrays that are deployed out of the end of trocar 1502 to at least partially encircle a target tissue 1510 upon deployment. The first set of electrodes 1504 and 1505 comprise stage 1 of the array, and the second set of electrodes 1506 and 1507 comprise stage 2 of the array. The stage 2 electrodes are mechanically coupled within the stage 1 electrodes and extend out of the stage 1 electrodes in a telescoping manner when deployed. The stage 1 electrodes 1504 and 1505 can be made out of round or elliptic tubing which can be formed to an appropriate shape and size to accommodate the inner, stage 2 electrodes. The stage 2 electrodes 1506 and 1507 can be made of round or flat wire to correspond with the inner dimensions and shape of the stage 1 electrodes.

Figure 15B:
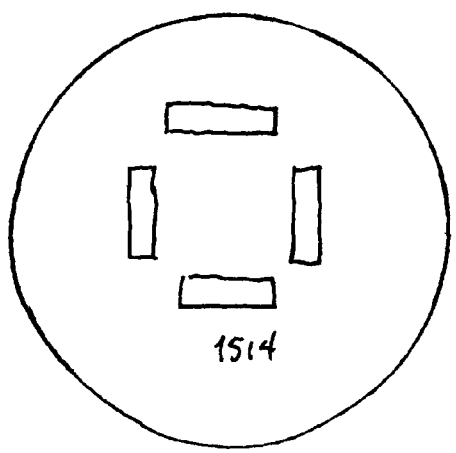
FIG. 15B illustrates an end view of the ablation device of FIG. 15A, under an embodiment.
Figure 15C:
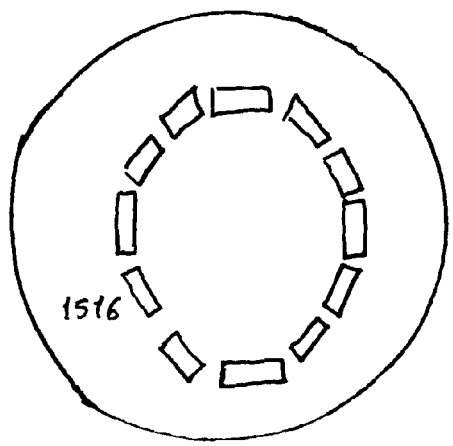
FIG. 15C illustrates an end view of the ablation device of FIG. 15A, under an alternative embodiment.

Any number of stage 1 and stage 2 electrodes can be configured to deploy out of the end of trocar 1502 to encircle the target tissue 1510 and produce an appropriate ablation pattern 1512. FIG. 15B illustrates an end view of the ablation device of FIG. 15A, under an embodiment in which four flat-wire electrodes 1514 in a square pattern deploy from the end of trocar 1502. FIG. 15C illustrates an end view of the ablation device of FIG. 15A, under an alternative embodiment in which twelve electrodes 1516 in a relatively circular pattern deploy from the end of trocar 1502. As can be seen from FIGS. 15B and 15C, as more electrodes are deployed, a more circular a pattern is produced around the end of the trocar, thus resulting in a more nearly spherical ablation pattern 1512 around the target tissue 1510.

Figures 16A, 16B:
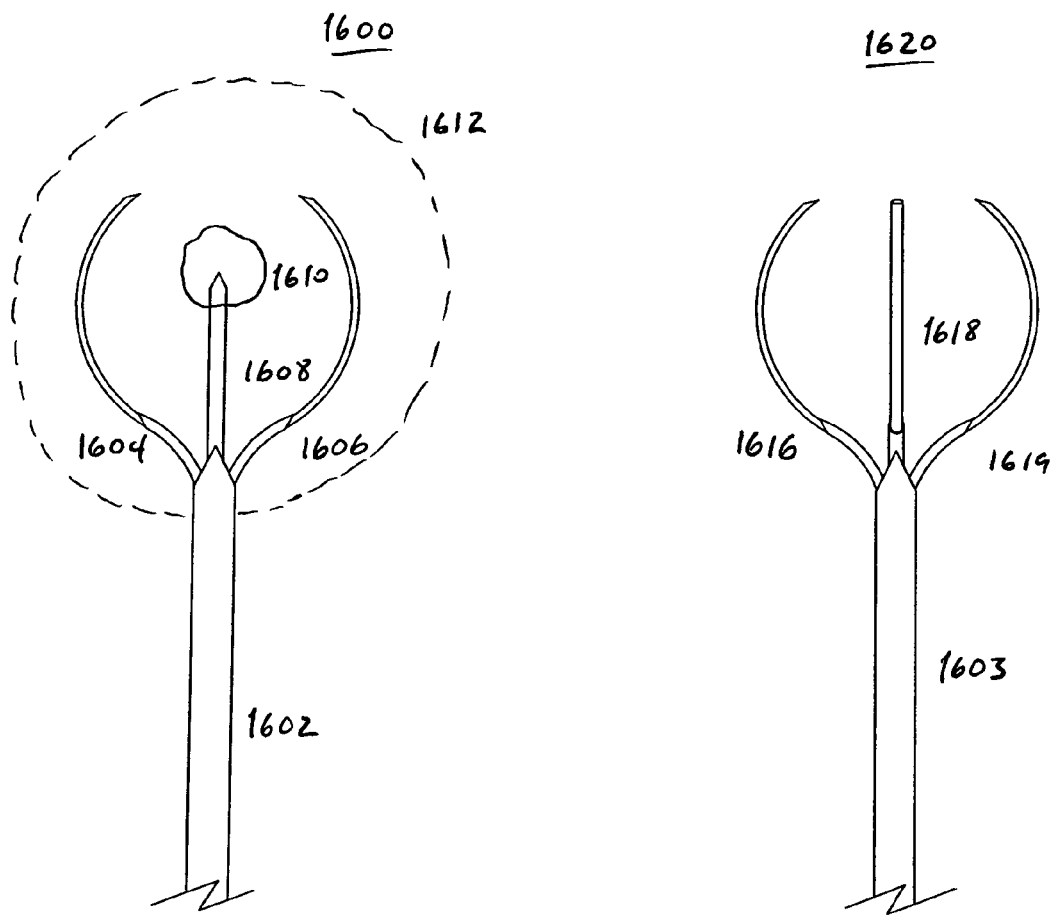
FIG. 16A illustrates an ablation device containing both surrounding electrodes and a penetrating electrode, according to an embodiment.
FIG. 16B illustrates an ablation device containing surrounding electrodes and a fluid delivery element, according to an embodiment.

FIG. 15A illustrates an embodiment in which the electrodes are configured to at least partially surround the target tissue. In an alternative embodiment, one or more electrodes may be configured to penetrate the target tissue, while other electrodes surround the tissue to produce the ablation pattern 1512. FIG. 16A illustrates an ablation device containing both surrounding electrodes and a penetrating electrode, according to an embodiment. In device 1600, electrodes 1604 and 1606 are configured to surround the target tissue 1610 upon deployment from trocar 1602 to form an ablation pattern 1612. A penetrating electrode 1608 deploys out of the distal end of trocar 1602 and includes a penetrating member for piercing target tissue 1610. The electrodes 1604, 1606 and 1608 can be configured as mono-polar or bi-polar electrodes to create a mono-polar or bi-polar device. One or more electrodes can also include a fluid delivery element for delivering fluid directly into target tissue. This is illustrated in FIG. 16B, in which trocar 1603 includes a fluid delivery element 1618. Element 1618 may be a delivery tube that is electrically neutral with respect to the other electrodes 1616 and 1619, it may be an electrode with a lumen, that is energized to a certain polarity relative to the other electrodes 1616 and 1619 and/or the body of the trocar 1603.

Figure 17:
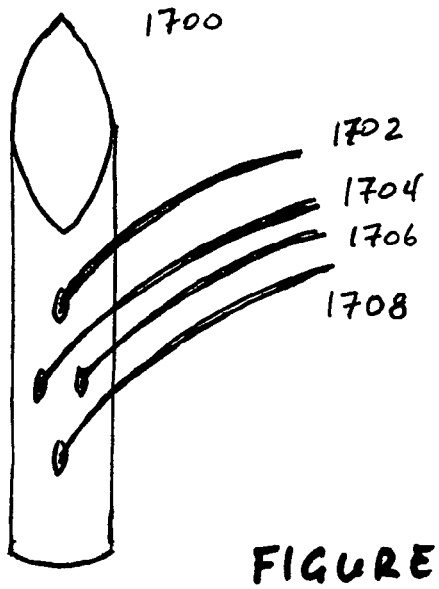
FIG. 17 is illustrates an ablation device with deployment of electrodes through the side of the trocar, under an embodiment.

In general, any number of separate surrounding electrodes can be configured to protrude from the side or the end of a trocar. FIG. 17 is illustrates an ablation device with deployment of electrodes through the side of the trocar. As shown in FIG. 17, the four electrodes 1702-1708 extend substantially laterally from the side of trocar 1700 from ports to at least partially surround a target tissue. The electrodes 1702-1708 can be electrically isolated from one another to form a bipolar system, and multiple combinations of electrode polarities can be created for bi-polar ablation. For example, the polarities of the four electrodes 1702, 1704, 1706, and 1708 can respectively be: +, +, −, −, or +, −, +, −, or −, −, +, +, or and so on. In one embodiment, the power generator coupled to the trocar 1700 can have multiple channels so that each electrode can have its own power level and associated impedance or thermo sensing capability. Based upon system feedback, the polarity of each electrode and the relative power level can be switched or changed by means of control circuits or software.

Figure 18:
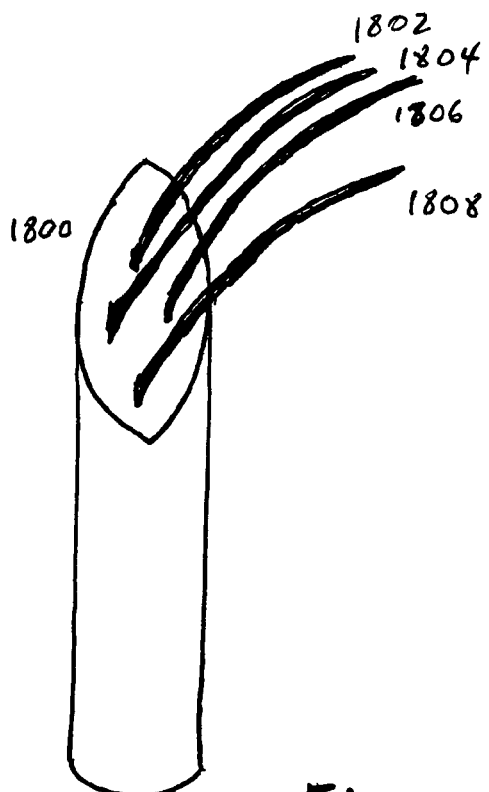
FIG. 18 is illustrates an ablation device with deployment of electrodes through an end of the trocar, under an embodiment.

In an alternative to the embodiment illustrated in FIG. 17, the electrodes can be configured to protrude from a distal end of the trocar. FIG. 18 illustrates an ablation device with deployment of electrodes through the end of the trocar. As shown in FIG. 18, the four electrodes 1802-1808 extend substantially laterally from the top of trocar 1800 from to at least partially surround a target tissue.

Figure 19A:
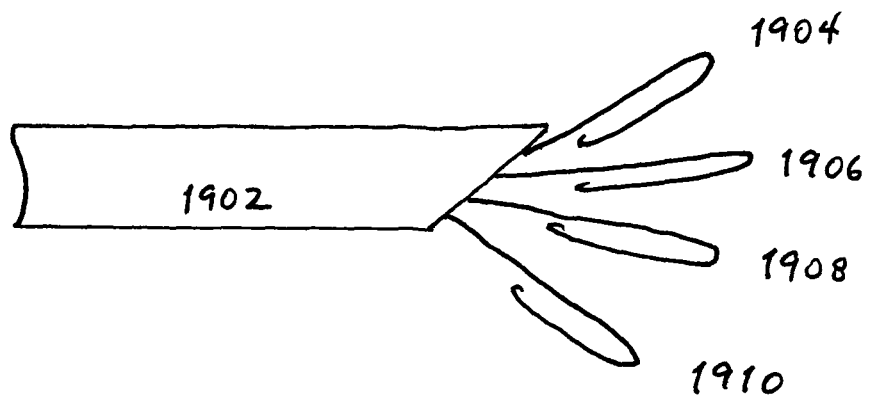
FIG. 19A is a side-view illustration of a trocar with spiral electrodes deployed from the end of the trocar, under an embodiment.
Figure 19B:
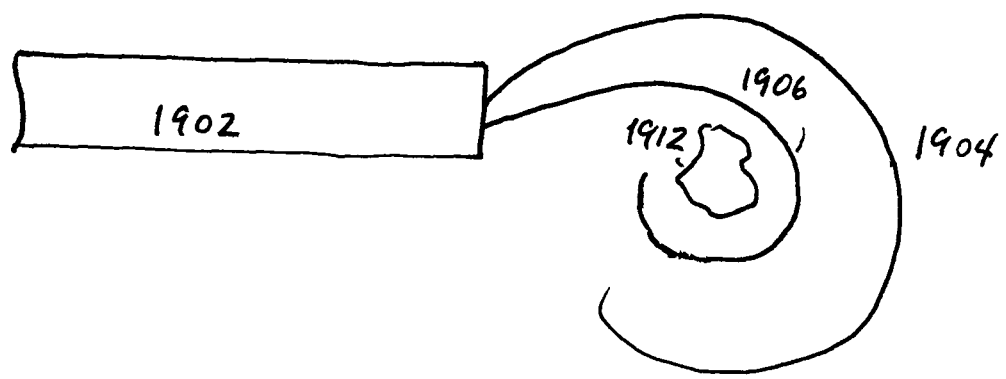
FIG. 19B is a top view of the embodiment of FIG. 19A showing the electrodes encircling a target tissue.

As shown in FIGS. 17 and 18, the electrodes may be relatively straight strips of metal deployed from the side or end of a trocar to surround a target tissue area. In some instances, more comprehensive encirclement of the target tissue can be accomplished through the use of curved or spiral-shaped electrodes. FIG. 19A is a side-view illustration of a trocar with spiral electrodes deployed from the end of the trocar, and FIG. 19B is a top view of the embodiment of FIG. 19A showing the electrodes encircling a target tissue. As shown in FIG. 19A, electrodes 1904-1910 extend outward from ports in the end of the trocar 1902. FIG. 19A illustrates device with four electrodes, although any number, such as between two and six electrodes could be shown. FIG. 19B is a top view that illustrates an example of how two of the electrodes 1904 and 1906 encircle a target tissue 1912. The spacing and length of the electrodes when deployed can be configured to accommodate specific applications. Also, as shown in FIG. 19B, the length and tightness of the spiral for each electrode can be different from one another, depending upon the specific need or application, as well. The polarity of the spiral electrodes can be set to positive or negative in a uniform or alternating manner, such as +, −, +, −, or +, +, −, −, etc. for electrodes 1904 to 1910, respectively.

Figure 20:
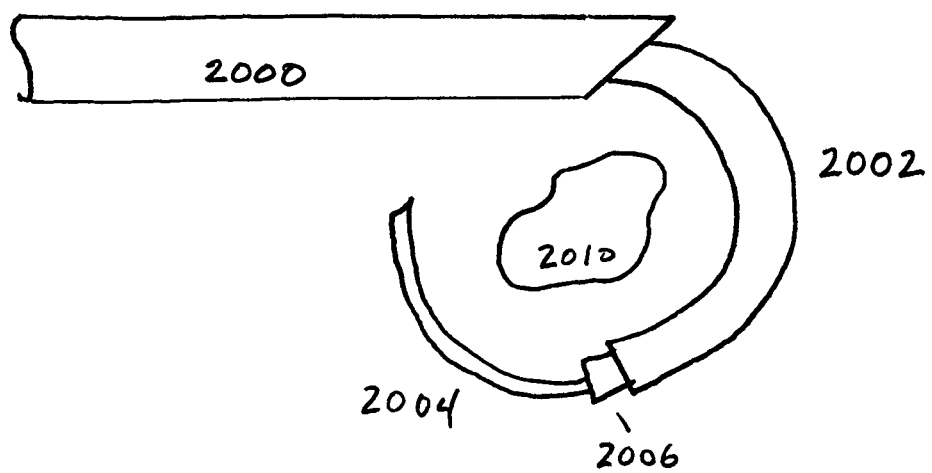
FIG. 20 illustrates a view of an ablation system that has a compound spiral electrode, under an embodiment.

For the embodiment illustrated in FIG. 19A, the electrodes were each shown as being single element electrodes. In an alternative embodiment, one or more of the electrodes may be a compound electrode comprising a first stage of one polarity and a second stage of the opposite polarity, as illustrated in the embodiment shown in FIG. 15A. For this embodiment, the second stage electrode can be housed within the first stage electrode through a physical coupling that maintains electrical isolation between the two nested electrodes. FIG. 20 illustrates an ablation device that has a compound spiral electrode, under an embodiment. In FIG. 20, a first stage electrode 2002 protrudes from the end of trocar 2000 when deployed. A second stage electrode 2004 is extended beyond electrode 2002 in a curved or spiral direction to encircle target tissue 2010. An insulative barrier 2006 electrically separates electrode 2002 from electrode 2004 to produce a bipolar device in which electrode 2002 is of a first polarity (e.g., positive) and electrode 2004 is of the opposite polarity (e.g., negative). Alternatively, electrode 2002 and electrode 2004 can protrude together from the end of trocar 2000 when deployed.

Figure 21:
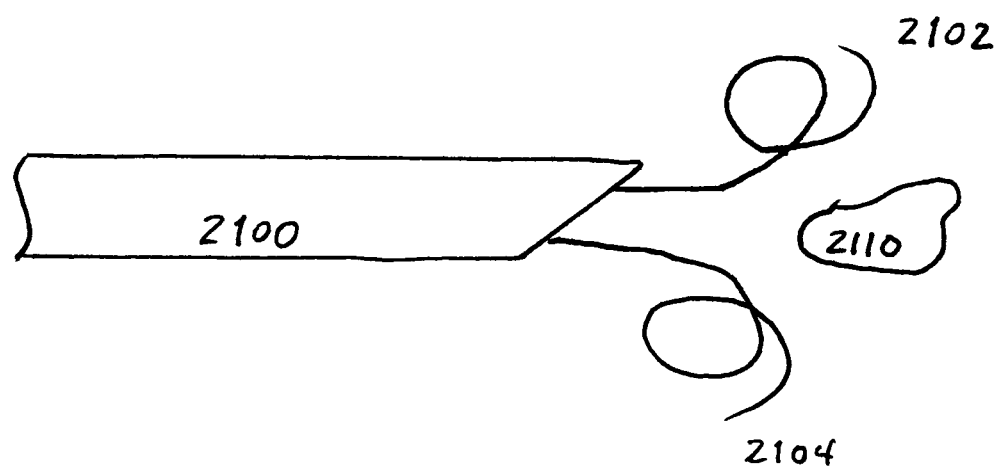
FIG. 21 illustrates a spiral electrode ablation device according to a second alternative embodiment.

FIG. 21 illustrates a spiral electrode ablation device according to a second alternative embodiment. For the embodiment illustrated in FIG. 21, two spiral electrodes 2102 and 2104 extend from the end of trocar 2100 when deployed. Instead of each electrode encircling target tissue 2110, they each encircle a side or plane of the target tissue such that together they create an ablation field that surrounds the target tissue. Each electrode alone creates a partially spherical pattern around a side of the target tissue. Together, they form a spherical or relatively spherical ablation pattern when energized. The electrodes used as illustrated in FIG. 21 can be of mono-polar or bi-polar configurations.

Although the embodiment illustrated in FIG. 21 illustrates two spiral electrodes, it should be noted that a greater number of electrodes of similar configuration (e.g., four or six) can be implemented to define an ablation field that surrounds the target tissue. In general, for any embodiment that includes spiral electrodes, it should be noted that the electrodes can be made from a material that allows them to be pre-formed, such as a shaped-memory metal, spring, flat wire, and so on.

Deployment of the electrodes for the embodiments illustrated in any of FIGS. 13-21 can be performed by an activation device in a handle coupled to an end of the trocar, such as that illustrated in FIG. 1. The electrode or electrodes in the device are coupled to a guide wire or other transport mechanism. The electrodes are deployed by advancing the guide wire outward and retracted by pulling the guide wire back into the trocar. A gear mechanism couples the activation unit such as a slider or knob (e.g., activator 104 in FIG. 1) to the guide wire, or similar push/pull rods that extend or retract the electrodes.

The devices shown in the embodiments of FIGS. 13-21 generally illustrate a single trocar device. In one embodiment, an ablation device containing multiple electrodes configured to surround or ablate a tissue volume can comprise more than one trocar, with each trocar containing one or more electrodes that surround the target tissue or a portion of the target tissue. The two or more trocars can be coupled to a single handle and activation device, or they can each be connected to their own handle and activation device. In general, a user manipulates both or all of the trocar bodies comprising a multi-trocar device to place the electrodes around the target tissue or within the tissue volume to create the intended ablation pattern.

Figure 22:
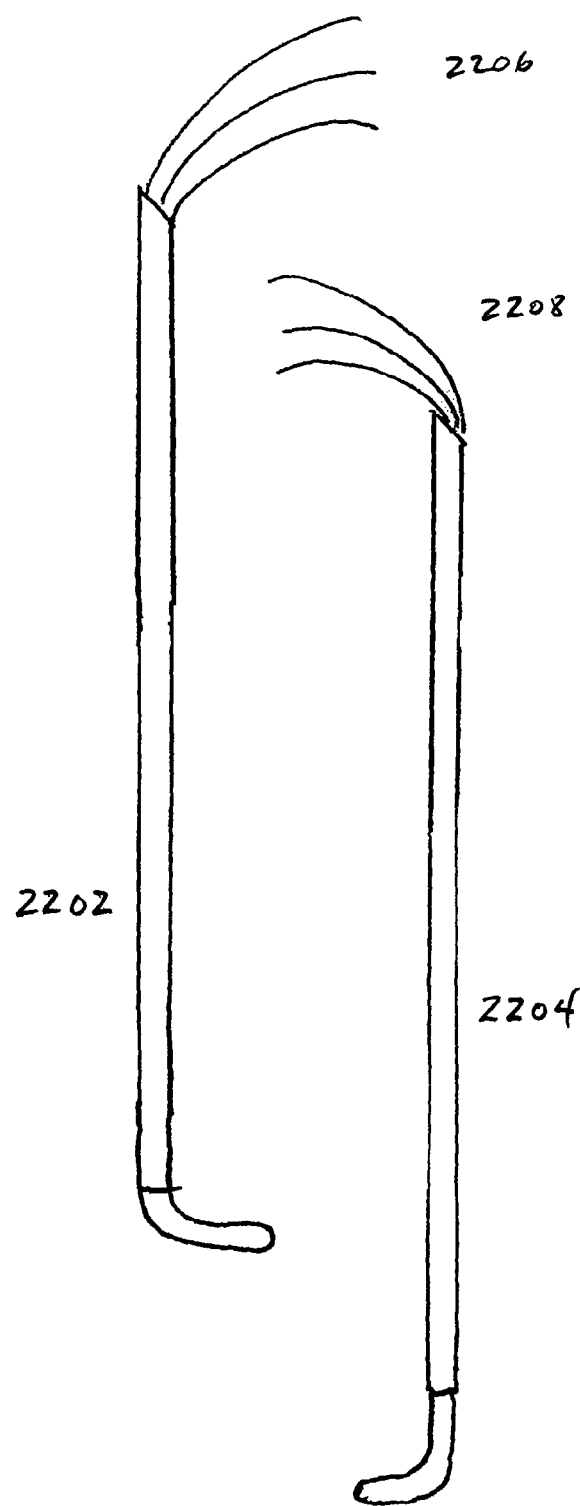
FIG. 22 illustrates a compound ablation device comprising two separate trocars for encircling a target tissue, under an embodiment.

FIG. 22 illustrates a compound ablation device comprising two separate trocar devices for encircling or partially encircling a target tissue or defining an ablation pattern, under an embodiment. Trocar 2202 and trocar 2204 are deployed in a side-by-side manner so that there respective electrode arrays 2206 and 2208 encircle a target tissue. The trocars can be rotated in any position relative to each other, as required, such as with the electrodes toward one another, as shown, away from one another, or any other direction relative to each other. The shape, length, composition and number of electrodes in the electrode arrays can be configured depending upon the application or characteristics of the target tissue. For example, the electrodes may be straight, such as shown in arrays 2206 and 2208. Alternatively, they may be spiral electrodes, or a combination of straight and spiral electrodes. Each independent trocar can have the same array configuration for a symmetrical system, or each can employ electrodes of different configurations for an asymmetrical system. The polarity of the arrays can be opposite to one another, such as shown in FIG. 22, in which electrode array 2206 is negatively charged and electrode array 2208 is positively charged, or they can each comprise electrodes of different polarities. In operation, the electrode arrays are configured to define an ablation field around a portion of the target tissue, so that together they form a complete or spherical ablation pattern encircling the target tissue. As shown in FIG. 22, each trocar is attached to its own respective handle that can include an activation device for deployment of the respective electrodes. Alternatively, the two trocar bodies 2202 and 2204 can be connected through a single handle for positioning and deployment of the electrodes.

In one embodiment, a guide structure can be provided that couples the trocar bodies, such as trocars 2202 and 2204 in a fixed orientation relative to one another. This stabilizes the trocars and allows the user to deploy the electrodes of the trocars independently without needing to hold the trocars laterally steady during deployment. The guide can be configured to allow the trocars to slide longitudinally relative to one another so that one can be extended further into the tissue relative to the other. The guide structure may further be configured to allow some movement of the trocar bodies closer to or further away from one another, or even to allow one trocar to pivot along an axis relative to the other trocar.

The electrode arrays for each trocar can extend from the end of the device or from the side of the device, as shown in FIGS. 17 and 18, or a combination of both. Furthermore, the electrodes in each array may be a single unit of a single polarity or a compound unit with one portion of a first polarity and a second portion of the opposite polarity.

Figure 23A:
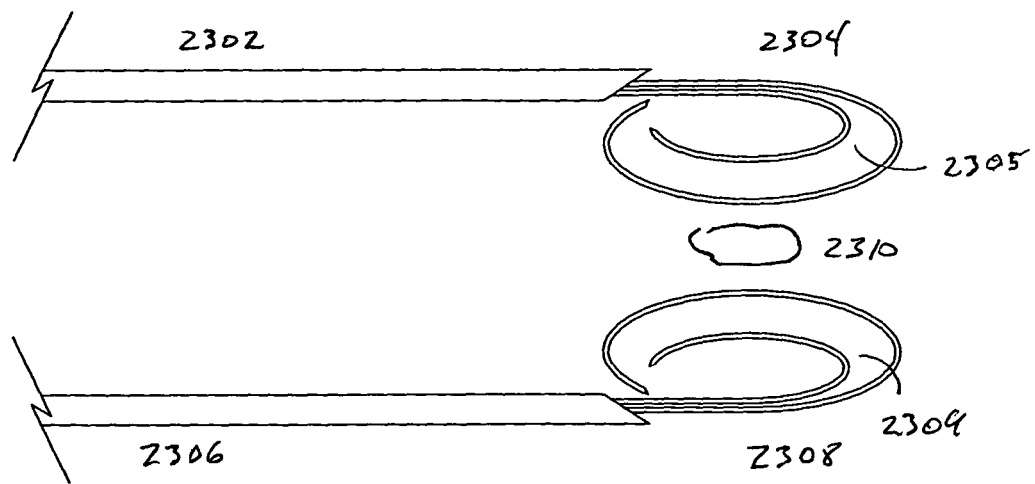
FIG. 23A is a side-view illustration of a compound ablation device with two separate trocars for encircling a target tissue, under an alternative embodiment.
Figure 23B:
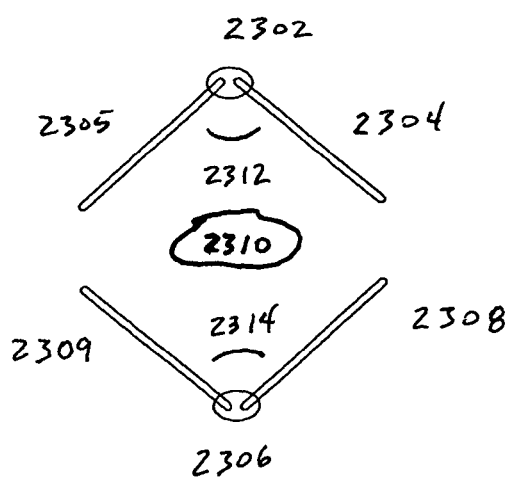
FIG. 23B is an end view of the alternative embodiment of FIG. 23A.

FIG. 23A illustrates a multi-trocar ablation device that utilizes one or more spiral electrodes in an array protruding from the distal end of each trocar. The device shown comprises a first trocar 2302 with two or more spiral electrodes 2304 and 2305 that extend from the end of the trocar at specific angles relative to the longitudinal axis of the trocar. A second trocar 2306 has two or more spiral electrodes 2308 and 2309 that likewise extend from the end of the trocar at specific angles relative to the longitudinal axis of the trocar. The angles of extension, as well as the electrode arrays are themselves shaped and configured so as to encircle target tissue 2310 and create a spherical or near-spherical ablation pattern in a tissue volume around the target tissue 2310. FIG. 23B is an end view of the multi-trocar ablation device of FIG. 23A. As shown in FIG. 23B, the electrodes 2304 and 2305 extend from the body of trocar 2302 at an angle 2312 relative to one another as defined by the longitudinal axis of the trocar, and the electrodes 2308 and 2309 extend from the body of trocar 2306 at an angle 2314 relative to one another as defined by the longitudinal axis of the trocar. The angle at which the electrode pairs are deployed relative to one another, as well as the electrode length, and tightness of spiral can be changed depending upon the actual application and characteristics of the target tissue 2310. The electrodes may each be of a single polarity with alternating polarity electrodes utilized in each pair or array of electrodes for each trocar, or they may be compound electrodes with sections of different polarities within each electrode. Thus, for example, for the embodiment illustrated in FIG. 23B, electrodes 2305 and 2309 can be both positively charged, with electrodes 2304 and 2308 both negatively charges, or electrodes 2305 and 2308 can be both positively charged, with electrodes 2304 and 2309 both negatively charged.

Figure 24A:
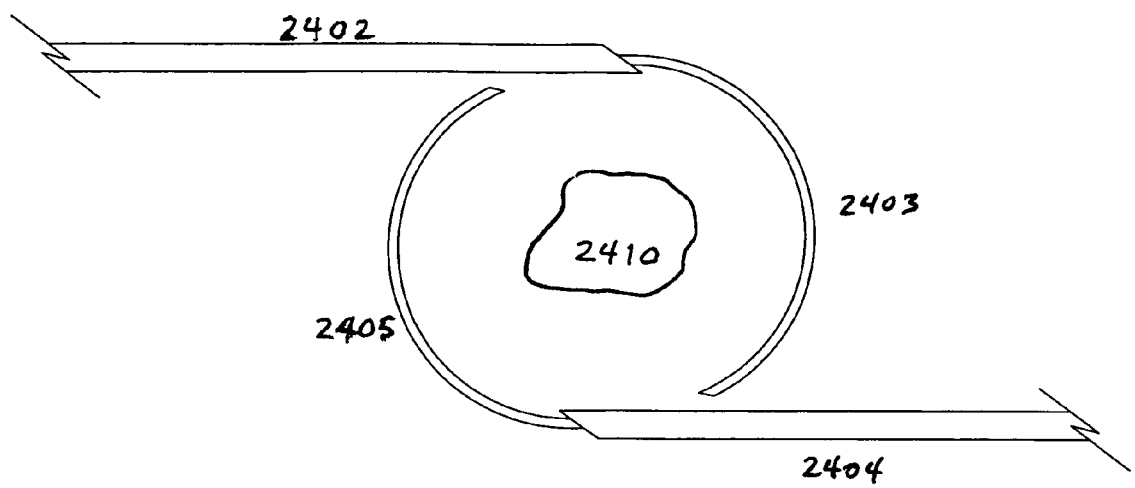
FIG. 24A illustrates a multi-trocar system comprising two single element electrode devices configured to at least partially surround a target tissue, under an embodiment.
Figure 24B:
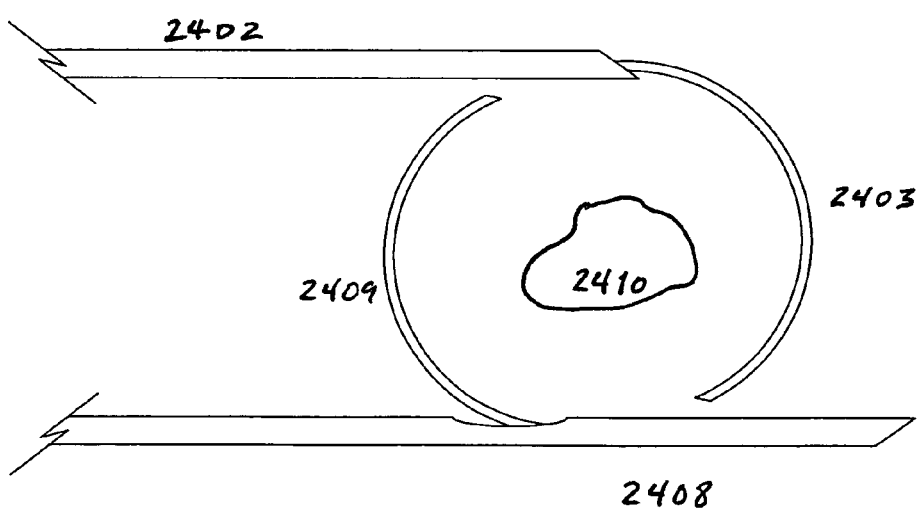
FIG. 24B illustrates an alternative embodiment of a multi-trocar system in which one electrode is deployed through the side of a trocar.

FIG. 24A illustrates a multi-trocar system comprising two single element electrode devices configured to at least partially surround a target tissue. The trocars of FIG. 24A are deployed in an opposing manner with trocar 2402 approaching target tissue 2410 from one side, and trocar 2404 approaching target tissue 2410 from the opposite side. The electrode 2403 is deployed from trocar 2402 to partially surround target tissue 2410 on one side and electrode 2405 is deployed from trocar 2404 to partially surround target tissue 2410 from the side opposite electrode 2403. Both electrodes set up a partially surrounding ablation pattern that together encompass target tissue 2410 in a spherical or relatively spherical ablation pattern. One or more of the electrodes can be deployed from the side of a trocar. FIG. 24B illustrates an alternative embodiment of a multi-trocar system in which one electrode is deployed through the side of a trocar. As shown in FIG. 24B, electrode 2409 is deployed through a port on the side of trocar 2408 which is placed in opposition to trocar 2402 relative to target tissue 2410.

The size, shape, number and orientation of electrodes deployed from the trocars illustrated in FIGS. 24A and 24B can be changed depending upon the shape, orientation, and position of the target tissue, as well as the point or points of entry relative to the target tissue or ablation area.

Although the embodiments of FIGS. 22 and 23A illustrate ablation systems comprising two separate trocar devices, it should be noted that greater than two trocars (e.g., three or four) may be used depending upon the application and characteristics of the target tissue. Furthermore, each of the trocars in a multi-trocar ablation device may use electrode arrays of different configurations to access and encircle difficult to reach target tissue areas or encircle target tissues of different sizes and configurations.

Figure 25A:
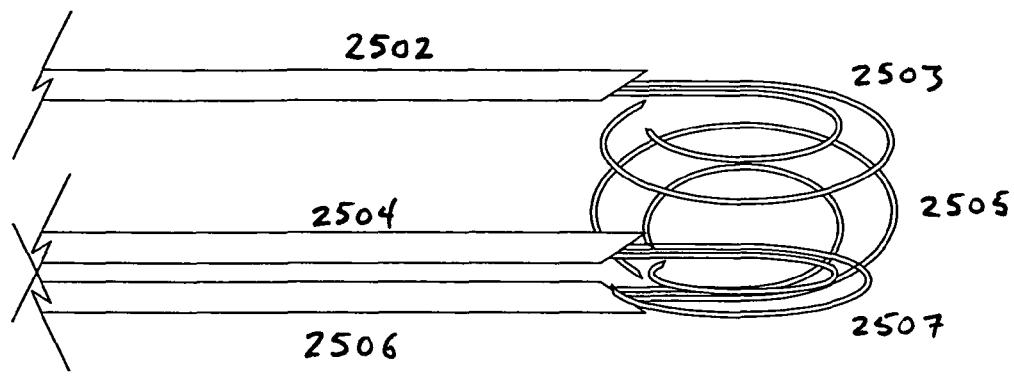
FIG. 25A illustrates a side-view of a three-trocar system configured to at least partially surround a target tissue, under an embodiment.
Figure 25B:
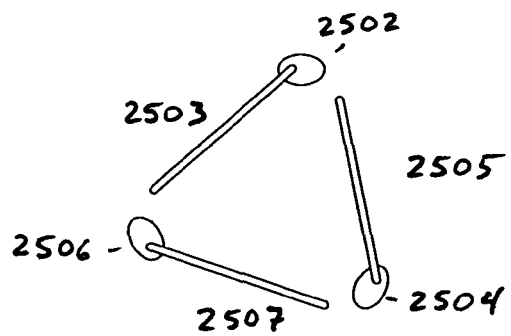
FIG. 25B illustrates an end-view of the three-trocar system illustrated in FIG. 25A.

FIG. 25A illustrates a side view of a three-trocar system configured to at least partially surround a target tissue, under an embodiment. Trocar 2502 deploys electrode array 2503, trocar 2504 deploys electrode array 2505, and trocar 2506 deploys electrode array 2507. The electrodes within each electrode array are shaped and oriented such that, when energized, the electrodes of each trocar create an ablation pattern that constitutes a partially spherical pattern. The three trocars are oriented around a target tissue or within an ablation area so that together their respective electrode arrays create a spherical or relatively spherical ablation pattern. FIG. 25B illustrates an end-view of the three-trocar system illustrated in FIG. 25A. As can be seen in FIG. 25B, the three electrode arrays are positioned in a roughly triangular orientation relative to one another so that a target tissue is surrounded, and/or a relatively spherical ablation pattern is produced. It should be noted that the electrodes shown in FIGS. 25A and 25B could be straight, spiral, single element, or compound, or any combination thereof. The composition and structure of the electrodes, as well as the polarity of the individual electrodes relative to one another or to the electrodes of any of the other trocars can be set to either positive or negative depending upon the requirements of the target tissue or area.

Although FIG. 25B illustrates the orientation of the three-trocar system in a triangular shape, it should be noted that any two or three of the trocars could be oriented in any position relative to one another so that their electrodes create a field sufficient to surround the target tissue or create the desired ablation pattern. For example, two trocars could be placed on either side of the target tissue to create an ablation pattern that is relatively spherical or an elongated sphere that substantially surrounds the target tissue. If the target tissue or area is sufficiently large, the trocars can be placed such that their respective electrode arrays are on opposite ends of the target tissue to ablate a portion or plane of the target tissue.

As described above, the tissue ablation system of an embodiment delivers energy to target tissue via the energy conduits or electrodes. The energy includes, for example, radio frequency (RF) energy, but is not so limited. For example, other types of energy can include microwave energy. The energy is delivered via any of a number of techniques. The energy can be applied via pulsed waveforms and/or continuous waveforms, but is not so limited.

In an example procedure that includes use of the tissue ablation system, energy can be applied to energy conduits during deployment of the energy conduits into the target tissue. The energy can be applied automatically or, alternatively, manually as a procedure progresses and as appropriate to the procedure. Also, the energy delivered to the target tissue can be adjusted during the procedure by adjusting any of the power level, the waveforms, and a combination of the power level and the waveform.

In another example procedure that includes use of the tissue ablation system, energy can be applied to energy conduits following deployment of the energy conduits into the target tissue. The energy can be applied automatically or, alternatively, manually as appropriate to the procedure. Also, the energy delivered to the target tissue can be adjusted manually and/or automatically during the procedure by adjusting any of the power level, the waveforms, and a combination of the power level and the waveform.

As described above, the application of power to the target tissue under an embodiment is controlled automatically and/or manually under a number of procedures. A first type of procedure uses a predetermined pattern of energy delivery according to a time schedule. A second type of procedure varies the application of energy to the target tissue volume in accordance with temperature information or feedback parameters of the tissue. A third type of procedure varies the application of energy to the target tissue volume in accordance with impedance information or feedback parameters of the tissue in combination with elapsed time. A fourth type of procedure varies the application of energy to the target tissue volume in accordance with impedance information or feedback parameters of the tissue. A fifth type of procedure varies the application of energy to the target tissue volume in accordance with temperature and impedance information or feedback parameters of the tissue.

It should be noted that patient and procedure selection is the responsibility of the medical professional/user and the outcome is dependent on many variables, including patient anatomy, pathology, and surgical techniques. Use of the tissue ablation device, system and methods described herein for tissue ablation can result in localized elevated temperatures that can cause thermal injury to the skin. In addition, tissue or organs adjacent to the tissue being ablated may be injured thermally. To minimize the potential for thermal injury to the skin or adjacent tissues, temperature-modifying measures can be initiated at the physician's discretion. These may include applying a sterile ice pack or saline-moistened gauze to cool and/or separate tissues, but are not so limited. The purpose of tissue ablation may be to destroy tissue within and around malignant tissue, such as tumors with cancer-causing cells.

The tissue ablation devices and methods described herein include a tissue ablation device, comprising an energy source; an introducer coupled to the energy source and having a body, a proximal end, and a distal end; and an electrode array coupled to the introducer and comprising a plurality of electrodes, each electrode of the plurality of electrodes configured to extend from the body of the introducer when moved from a retracted state to a deployed state, and configured to at least partially encircle an intended ablation that will at least partially encompass a target tissue when extended in the deployed state and to form a relatively spherical shaped ablation pattern in a tissue volume surrounding the target tissue when energized by the energy source.

A tissue ablation device of embodiments include electrodes that extend longitudinally from the distal end of the body of the introducer or laterally from the body of the introducer.

The energy source of an embodiment includes a radio frequency (RF) generator.

The tissue ablation devices and methods described herein include an array of bipolar electrodes configured to be coupled to an energy source, wherein the array is configured to encircle at least a portion of a target tissue and create a relatively spherical ablation pattern around a tissue volume including the target tissue, and ablate the target tissue from an outside surface of the target tissue to an inner portion of the target tissue when the electrodes are energized by the energy source.

The system of an embodiment further comprises a controller coupled among the RF generator and the bipolar electrodes to provide automatic control of energy delivery to each of the bipolar electrodes.

The bipolar electrodes in an embodiment comprise spiral metal strips, and the electrode array comprises two or more spiral metal strips arranged in an alternating polarity series that includes at least one bipolar electrode of a first polarity in series with at least one bipolar electrode of a second polarity.

The tissue ablation device of an embodiment comprises two or more introducers coupled to a single handle and activation mechanism that allows a user to deploy or retract the electrode array.

The tissue ablation device of an alternative embodiment comprises two or more introducers coupled to respective handles and activation mechanisms that allows a user to deploy or retract a respective portion of the electrode array coupled to each introducer.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above description of illustrated embodiments of the tissue ablation devices and methods is not intended to be exhaustive or to limit the systems and methods to the precise form disclosed. While specific embodiments of, and examples for, the tissue ablation devices and methods are described herein for illustrative purposes, various equivalent modifications are possible within the scope of the systems and methods, as those skilled in the relevant art will recognize. The teachings of the tissue ablation devices and methods provided herein can be applied to other medical systems, not only for the medical systems described above.

The elements and acts of the various embodiments described above can be combined to provide further embodiments. These and other changes can be made to the tissue ablation devices and methods in light of the above detailed description. As an example, following are one or more examples of additional embodiments of the tissue ablation devices, each of which may be used alone or in combination with other embodiments described herein.

The tissue ablation devices and methods further include allowing the device intended to create an ablation in tissue to surround, encompass, or otherwise create a three dimensional perimeter around a volume of tissue, such as a tumor, without penetrating or going through the such volume.

The tissue ablation devices and methods further include the ability and method in either a mono-polar or bi-polar configuration for a device to switch between various electrodes thereby creating different groups of active electrodes and creating different paths of current flow after the application of energy to the target tissue.

The tissue ablation devices and methods further include the ability and method in either a mono-polar or bi-polar configuration for a device to switch between various electrodes thereby creating different groups of active electrodes and creating different paths of current flow after the application of energy to the target tissue, and/or to continue to switch in any combination and for any number of times.

The tissue ablation devices and methods further include the ability and method in either a mono-polar or bi-polar configuration for a device to switch between various electrodes thereby creating different groups of active electrodes and creating different paths of current flow after the application of energy to the target tissue, and/or to continue to switch in any combination and for any number of times, and/or the ability to switch on the fly with or without the reduction of applied power.

The tissue ablation devices and methods further include the ability and method in either a mono-polar or bi-polar configuration for a device to switch between various electrodes thereby creating different groups of active electrodes and creating different paths of current flow after the application of energy to the target tissue, and/or to continue to switch in any combination and for any number of times, and/or the ability to switch on the fly with or without the reduction of applied power, and/or to alter the applied energy prior to switching.

The tissue ablation devices and methods further include the ability and method in either a mono-polar or bi-polar configuration for a device to switch between various electrodes thereby creating different groups of active electrodes and creating different paths of current flow after the application of energy to the target tissue, and/or to continue to switch in any combination and for any number of times, and/or the ability to switch on the fly with or without the reduction of applied power, and/or to alter the applied energy prior to switching, and/or to switch based on fixed or changing tissue characteristics including, but not limited to, tissue temperature, impedance, rate of change of temperature, rate of change of impedance, and the like.

The tissue ablation devices and methods further include using electrode coatings or other means to locally lower the impedance around them without significantly reducing the impedance a large (several electrode diameters or width) distance away from the electrode; e.g., application of energy in such a way and for the purpose of releasing conductive interstitial cellular fluid or a coating of salt crystals on the electrodes.

The tissue ablation devices and methods further include applying energy followed by a reduction or dwell time followed by the application or reapplication of energy to aid in the application of higher amounts of energy. This may be performed using various wave forms for example saw-tooth, square wave, and the like including, but not limited to, the controlling the delivery of energy to a level at or near zero (0).

The tissue ablation devices and methods further include applying energy followed by a reduction or dwell time followed by the application or reapplication of energy to aid in the application of higher amounts of energy. This may be performed using various wave forms for example saw-tooth, square wave, and the like including, but not limited to, the controlling the delivery of energy to a level at or near zero (0), and/or where the energy delivered is reduced or eliminated with/at approximately the same time the energy is increased between other electrodes or electrode pairs or some of the current and some other electrodes within the device.

The tissue ablation devices and methods further include applying energy followed by a reduction or dwell time followed by the application or reapplication of energy to aid in the application of higher amounts of energy. This may be performed using various wave forms for example saw-tooth, square wave, and the like including, but not limited to, the controlling the delivery of energy to a level at or near zero (0), and/or where the energy delivered is reduced or eliminated with/at approximately the same time the energy is increased between other electrodes or electrode pairs or some of the current and some other electrodes within the device, for any combinations, durations, fixed or varying power levels, and for any duration or number of cycles.

The tissue ablation devices and methods further include the use of high energy levels that are otherwise unsustainable due to the increase in tissue impedance or tissue char followed by a reduction in delivered energy that includes a reduction or dwell time followed by the application or reapplication of energy to aid in the application of higher amounts of energy. This may be performed using various wave forms for example saw-tooth, square wave, and the like including, but not limited to, the controlling the delivery of energy to a level at or near zero (0).

The tissue ablation devices and methods further include the ability to change the deployment shape of the electrodes to, for example, be able to alter the diameter of the deployed electrodes resulting in various sizes of ablative tissue (e.g., 3 cm diameter, 5 cm diameter, 7.5 cm diameter, and 15 cm diameter) by means of elements that are pulled ("pull wires"), pushed ("push wires"), differential heating and subsequent expansion of off-axis elements to name a few.

The tissue ablation devices and methods further include allowing the device intended to create an ablation in tissue to surround, encompass, or otherwise create a three dimensional perimeter around a volume of tissue, such as a tumor, without penetrating or going through the such volume, where the electrode configuration creates a nominal predefined shape when used a predefined way.

The elements and acts of the various embodiments described above can be combined to provide further embodiments. These and other changes can be made to the thermal ablation methods and devices in light of the above detailed description.

What is claimed is:

1. A tissue ablation device, comprising:
an array of bipolar electrodes configured to be coupled to an energy source, wherein the array of bipolar electrodes comprises at least one electrode forming a semi-spherical electrode in a deployed state, wherein the at least one electrode comprises a first portion having a first polarity and a second portion having a second polarity that is different from the first polarity, wherein the first portion is coupled to the second portion by extending through an insulative member to form the semi-spherical electrode when deployed;
wherein the array of bipolar electrodes is configured to at least partially encircle a portion of an intended ablation that will at least partially encompass a target tissue and create an ablation pattern around a tissue volume including the target tissue, and ablate the target tissue from an outside surface of the target tissue to an inner portion of the target tissue when the array of bipolar electrodes is energized by the energy source.

2. The tissue ablation device of claim 1, wherein the ablation pattern comprises one of a generally spherical pattern, an elongated spherical pattern, and a closed compound curve pattern.

3. The tissue ablation device of claim 2, wherein the energy source coupled to the array of bipolar electrodes produces energy of alternating polarity.

4. The tissue ablation device of claim 2, wherein the array of bipolar electrodes comprises a penetrating electrode configured to penetrate a surface of the target tissue upon advancement from the array of bipolar electrodes.

5. A method of ablating tissue, comprising:
placing a first electrode array around a first portion of a target tissue, wherein the first electrode array comprises at least one first electrode forming a first semi-spherical electrode in a deployed state;
placing a second electrode array around a second portion of the target tissue, wherein the second electrode array comprises at least one second electrode forming a second semi-spherical electrode in a deployed state, wherein at least one of the at least one first electrode and the at least one second electrode comprises a first portion having a first polarity and a second portion having a second polarity that is different from the first polarity, wherein the first portion is coupled to the second portion by extending through an insulative member to form the semi-spherical electrode when deployed;
energizing the first electrode array and the second electrode array to form an ablation pattern around a tissue volume including the target tissue; and
applying sufficient energy to the first and second electrode arrays to ablate the target tissue from an outer surface to an inner portion of the target tissue.

6. The method of claim 5, wherein the ablation pattern comprises one of a generally spherical pattern, an elongated spherical pattern, and a closed compound curve pattern.

7. The method of claim 6, wherein the first electrode array comprises one or more individual electrodes that are deployed along a first plane of the device, wherein the at least one first electrode comprises the one or more individual electrodes along the first plane and the second electrode array comprises one or more individual electrodes that are deployed along a second plane of the device, wherein the at least one second electrode comprises the one or more individual electrodes along the second plane.

8. The method of claim 7, wherein the first electrode array and the second electrode array are contained in a single introducer device, and are deployed through an activation device coupled to a handle coupled to the introducer device.

9. The method of claim 6, wherein energizing the first electrode array and the second electrode array comprises applying radio frequency energy through the first electrode array and the second electrode array.

10. The method of claim 9, further comprising applying alternating polarity to the one or more electrodes of the first electrode array and the one or more electrodes of the second electrode array.

11. A device for creating ablations in tissue, comprising:
a trocar assembly;
a handle assembly with an activation device integral therewith and coupled to the trocar assembly; and
a planar electrode assembly coupled to the trocar assembly, and configured to be coupled to an energy source, and extendable to a deployed position from a retracted position within the trocar assembly upon activation of the activation device, the planar electrode assembly consisting of one or more individual electrodes that together circumscribe a relatively spherical ablation pattern in the tissue upon application of energy from the energy source, wherein at least one electrode of the one or more individual electrodes forms a semi-spherical electrode in a deployed state and comprises a first portion having a first polarity and a second portion having a second polarity that is different from the first polarity, wherein the first portion is coupled to the second portion by extending through an insulative member to form the semi-spherical electrode when deployed.

12. The device of claim 11, wherein one or more individual electrodes extend from the trocar assembly, each electrode of the one or more individual electrodes forming a semi-elliptical electrode.

13. The device of claim 11, wherein the relatively spherical ablation pattern comprises an elongated spherical ablation pattern.

14. The device of claim 11, wherein the energy source is configured to generate energy of alternating polarity to the planar electrode assembly.

15. The device of claim 14, wherein the energy source produces radio frequency energy.

* * * * *